(12) United States Patent
Shao et al.

(10) Patent No.: US 6,939,700 B2
(45) Date of Patent: Sep. 6, 2005

(54) ISOLATED HUMAN AMINOACYLASE, NUCLEIC ACID MOLECULES ENCODING HUMAN AMINOACYLASE, AND USES THEREOF

(75) Inventors: Wei Shao, Frederick, MD (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 13 days.

(21) Appl. No.: 10/109,860

(22) Filed: Apr. 1, 2002

(65) Prior Publication Data

US 2002/0142421 A1 Oct. 3, 2002

Related U.S. Application Data

(62) Division of application No. 09/814,951, filed on Mar. 23, 2001, now Pat. No. 6,387,661.

(51) Int. Cl.[7] .................................................. C12N 9/14
(52) U.S. Cl. ........................ 435/195; 435/183; 530/350; 536/23.1; 536/23.2
(58) Field of Search ................................. 435/183, 145; 530/350; 536/23.1, 23.2

(56) References Cited

U.S. PATENT DOCUMENTS 5,498,697 A    3/1996   Iwaki et al. ................ 530/350

OTHER PUBLICATIONS

Cook et al., Human Aminoacylase–1, Journal of Biological Chemistry, vol 268 (23), Aug. 1993, pp. 17010–17017.*
Biagini et al., Sequence analysis of the aminoacylase–1 family. A new proposed signature for metalloexopeptidases, Comparative Biochemistry and Physiology, vol. 128, 2001, pp. 469–481.*
Iwaki et al. "Protein, DNA Coding Said Protein, and Preparation of Said Protein." Database Patent AA, US–08–127–278–4, Mar. 12, 1996.
International Search report dated Aug. 26, 2003.
Results of BLAST search of SEQ ID No:2 against Derwent (FastAlert and GeneSeqP) and NCBI (pataa) protein patent database on Aug. 29, 2003.
Mitta M. et al.; "The Nucleotide Sequence Of Human Aminoacylase–1"; Biochimica et Biophysica ACTA, Amsterdam, NL, vol. 1174, No. 2, Aug. 19, 1993, pp. 201–203, XP002300973; ISSN: 0006–3002.
Copy of Supplementary Partial European Search Report dated Feb. 15, 2005.

* cited by examiner

*Primary Examiner*—Richard Hutson
(74) *Attorney, Agent, or Firm*—Celera Genomics; Lin Sun-Hoffman

(57) ABSTRACT

The present invention provides amino acid sequences of peptides that are encoded by genes within the human genome, the enzyme peptides of the present invention. The present invention specifically provides isolated peptide and nucleic acid molecules, methods of identifying orthologs and paralogs of the enzyme peptides, and methods of identifying modulators of the enzyme peptides.

4 Claims, 10 Drawing Sheets

```
  1 CTGCGACCTC GCAGGCGACC TCGCTGGACC CTAAGTCCAG GCCACAGTCA
 51 GGGAAGGGCG CTGAGAGGCG AGCGTGAGCC CAGCGACAGG AGAGTGAGCT
101 CACCACGCGC AGCGCCATGA CCAGCAAGGG TCCCGAGGAG GAGCACCCAT
151 CGGTGACGCT CTTCCGCCAG TACCTGCGTA TCCGCACTGT CCAGCCCAAG
201 CCTGACTATG GCACCAACCC TACACTCTCC TCCATCTTGC TCAACTCCCA
251 CACGGATGTG GTGCCTGTCT TCAAGGAACA TTGGAGTCAC GACCCCTTTG
301 AGGCCTTCAA GGATTCTGAG GGCTACATCT ATGCCAGGGG TGCCCAGGAC
351 ATGAAGTGCG TCAGCATCCA GTACCTGGAA GCTGTGAGGA GGCTGAAGGT
401 GGAGGCCAC CGGTTCCCCA GAACCATCCA CATGACCTTT GTGCCTGATG
451 AGGAGGTTGG GGGTCACCAA GGCATGGAGC TGTTCGTGCA GCGGCCTGAG
501 TTCCACGCCC TGAGGGCAGG CTTTGCCCTG GATGAGGGCA TAGCCAATCC
551 CACTGATGCC TTCACTGTCT TTTATAGTGA GCGGAGTCCC TGGTGGGTGC
601 GGGTTACCAG CACTGGGAGG CCAGGCCATG CCTCACGCTT CATGGAGGAC
651 ACAGCAGCAG AGAAGCTGCA CAAGGTTGTA AACTCCATCC TGGCATTCCG
701 GGAGAAGGAA TGGCAGAGGC TGCAGTCAAA CCCCCACCTG AAAGAGGGGT
751 CCGTGACCTC CGTGAACCTG ACTAAGCTAG AGGGTGGCGT GGCCTATAAC
801 GTGATACCTG CCACCATGAG CGCCAGCTTT GACTTCCGTG TGGCACCGGA
851 TGTGGACTTC AAGGCTTTTG AGGAGCAGCT GCAGAGCTGG TGCCAGGCAG
901 CTGGCGAGGG GGTCACCCTA GAGTTTGCTC AGAAGTGGAT GCACCCCCAA
951 GTGACACCTA CTGATGACTC AAACCCTTGG TGGGCAGCTT TTAGCCGGGT
1001 CTGCAAGGAT ATGAACCTCA CTCTGGAGCC TGAGATCATG CCTGCTGCCA
1051 CTGACAACCG CTATATCCGC GCGGTGGGGG TCCAGCTCT AGGCTTCTCA
1101 CCCATGAACC GCACACCTGT GCTGCTGCAC GACCACGATG AACGGCTGCA
1151 TGAGGCTGTG TTCCTCCGTG GGGTGGACAT ATATACACGC CTGCTGCCTG
1201 CCCTTGCCAG TGTGCCTGCC CTGCCCAGTG ACAGCTGAGC CCTGGAACTC
1251 CTAAACCTTT GCCCCTGGGG CTTCCATCCC AACCAGTGCC AAGGACCTCC
1301 TCTTCCCCCT TCCAAATAAT AAAGTCTATG GACAGGGCTG TCTCTGAAGT
1351 ACTAACACAA AAAAAAAAAA AAAAAAAAAA AAAAAAAAAA AAAAAAAAAA
1401 AAAAAAAAAA AAAAAAAAAA AAAAAAAAAA AAAAAAAAAA AAAAA
(SEQ ID NO:1)
```

FEATURES:
5'UTR:        1 - 116
Start Codon:  117
Stop Codon:   1236
3'UTR:        1239

Homologous proteins:
Top 10 BLAST Hits:

```
                                                                     Score    E
Sequences producing significant alignments:                          (bits)   value CRA|18000004920175 /altid=gi|4501901  /def=ref|NP_000657.1| amin...   760   0.0
CRA|98000043609872 /altid=gi|12832397 /def=dbj|BAB22090.1|  (AKO...   663   0.0
CRA|18000004882854 /altid=gi|584724   /def=sp|P37111|ACY1_PIG AMI...  657   0.0
CRA|18000004885324 /altid=gi|284560   /def=pir||S27010 aminoacyla...  651   0.0
CRA|105000014651331 /altid=gi|10726439 /def=gb|AAG22139.1|  (AEO...   369   e-101
CRA|18000005180707 /altid=gi|7495817  /def=pir||T19180 hypotheti...   346   3e-94
CRA|18000005180709 /altid=gi|7495818  /def=pir||T19182 hypotheti...   343   2e-93
CRA|18000005180708 /altid=gi|7495819  /def=pir||T19181 hypotheti...   337   1e-91
CRA|89000000202498 /altid=gi|7300958  /def=gb|AAF56097.1|  (AE003...   332   6e-90
CRA|89000000202496 /altid=gi|7300956  /def=gb|AAF56095.1|  (AE003...   329   4e-89
```

FIGURE 1A

EST:

Sequences producing significant alignments:

| | Score (bits) | E Value |
|---|---|---|
| gi\|12943613 /dataset=dbest /taxon=960... | 1760 | 0.0 |
| gi\|12945798 /dataset=dbest /taxon=960... | 1473 | 0.0 |
| gi\|10155686 /dataset=dbest /taxon=96... | 1308 | 0.0 |
| gi\|12781232 /dataset=dbest /taxon=960... | 1304 | 0.0 |
| gi\|10216357 /dataset=dbest /taxon=96... | 973 | 0.0 |

EXPRESSION INFORMATION FOR MODULATORY USE:
gi|12943613   placenta
gi|12945798   T cells from T cell leukemia
gi|10155686   ovary
gi|12781232   brain
gi|10216357   lung Tissue Expression:
leukocyte

FIGURE 1B

```
  1 MTSKGPEEEH PSVTLFRQYL RIRTVQPKPD YGTNPTLSSI LLNSHTDVVP
 51 VFKEHWSHDP FEAFKDSEGY IYARGAQDMK CVSIQYLEAV RRLKVEGHRF
101 PRTIHMTFVP DEEVGGHQGM ELFVQRPEFH ALRAGFALDE GIANPTDAFT
151 VFYSERSPWW VRVTSTGRPG HASRFMEDTA AEKLHKVVNS ILAFREKEWQ
201 RLQSNPHLKE GSVTSVNLTK LEGGVAYNVI PATMSASFDF RVAPDVDFKA
251 FEEQLQSWCQ AAGEGVTLEF AQKWMHPQVT PTDDSNPWWA AFSRVCKDMN
301 LTLEPEIMPA ATDNRYIRAV GVPALGFSPM NRTPVLLHDH DERLHEAVFL
351 RGVDIYTRLL PALASVPALP SDS
    (SEQ ID NO:2)
```

FEATURES:
Functional domains and key regions:
[1] PDOC00001 PS00001 ASN_GLYCOSYLATION
N-glycosylation site Number of matches: 2
    1    217-220 NLTK (SEQ ID NO: 15)
    2    300-303 NLTL (SEQ ID NO: 16)

---

[2] PDOC00005 PS00005 PKC_PHOSPHO_SITE
Protein kinase C phosphorylation site

Number of matches: 3
    1    2-4 TSK
    2    154-156 SER
    3    166-168 TGR

---

[3] PDOC00006 PS00006 CK2_PHOSPHO_SITE
Casein kinase II phosphorylation site

Number of matches: 4
    1    44-47 SHTD (SEQ ID NO: 17)
    2    179-182 TAAE (SEQ ID NO: 18)
    3    219-222 TKLE (SEQ ID NO: 19)
    4    280-283 TPTD (SEQ ID NO: 20)

---

[4] PDOC00007 PS00007 TYR_PHOSPHO_SITE
Tyrosine kinase phosphorylation site
        65-72 KDSEGYIY (SEQ ID NO: 21)

---

[5] PDOC00008 PS00008 MYRISTYL
N-myristoylation site
Number of matches: 4
    1    32-37 GTNPTL (SEQ ID NO: 22)
    2    115-120 GGHQGM (SEQ ID NO: 23)
    3    211-216 GSVTSV (SEQ ID NO: 24)
    4    224-229 GVAYNV (SEQ ID NO: 25)

---

[6] PDOC00613 PS00758 ARGE_DAPE_CPG2_1
ArgE / dapE / ACY1 / CPG2 / yscS family signature 1

40-49 ILLNSHTDVV (SEQ ID NO: 26)

---

[7] PDOC00613 PS00759 ARGE_DAPE_CPG2_2
ArgE / dapE / ACY1 / CPG2 / yscS family signature 2

76-115 AQDMKCVSIQYLEAVRRLKVEGHRFPRTIHMTFVPDEEVG (SEQ ID NO:27)

Membrane spanning structure and domains:
Candidate membrane-spanning segments:
  Helix Begin  End  Score Certainty
    1  220  240  0.606 Putative

FIGURE 2A

BLAST Alignment to Top Hit:
>CRA|180000004920175 /altid=gi|4501901 /def=ref|NP_000657.1|
        aminoacylase 1 [Homo sapiens] /org=Homo sapiens
        /taxon=9606 /dataset=nraa /length=408
        Length = 408

Score = 760 bits (1941), Expect = 0.0
Identities = 373/408 (91%), Positives = 373/408 (91%), Gaps = 35/408 (8%)

```
Query:   1  MTSKGPEEEHPSVTLFRQYLRIRTVQPKPDYG------------------------------ 32
            MTSKGPEEEHPSVTLFRQYLRIRTVQPKPDYG
Sbjct:   1  MTSKGPEEEHPSVTLFRQYLRIRTVQPKPDYGAAVAFFEETARQLGLGCQKVEVAPGYVV  60

Query:  33  -------TNPTLSSILLNSHTDVVPVFKEHWSHDPFEAFKDSEGYIYARGAQDMKCVSIQ  85
                   TNPTLSSILLNSHTDVVPVFKEHWSHDPFEAFKDSEGYIYARGAQDMKCVSIQ
Sbjct:  61  TVLTWPGTNPTLSSILLNSHTDVVPVFKEHWSHDPFEAFKDSEGYIYARGAQDMKCVSIQ 120

Query:  86  YLEAVRRLKVEGHRFPRTIHMTFVPDEEVGGHQGMELFVQRPEFHALRAGFALDEGIANP 145
            YLEAVRRLKVEGHRFPRTIHMTFVPDEEVGGHQGMELFVQRPEFHALRAGFALDEGIANP
Sbjct: 121  YLEAVRRLKVEGHRFPRTIHMTFVPDEEVGGHQGMELFVQRPEFHALRAGFALDEGIANP 180

Query: 146  TDAFTVFYSERSPWWVRVTSTGRPGHASRFMEDTAAEKLHKVVNSILAFREKEWQRLQSN 205
            TDAFTVFYSERSPWWVRVTSTGRPGHASRFMEDTAAEKLHKVVNSILAFREKEWQRLQSN
Sbjct: 181  TDAFTVFYSERSPWWVRVTSTGRPGHASRFMEDTAAEKLHKVVNSILAFREKEWQRLQSN 240

Query: 206  PHLKEGSVTSVNLTKLEGGVAYNVIPATMSASFDFRVAPDVDFKAFEEQLQSWCQAAGEG 265
            PHLKEGSVTSVNLTKLEGGVAYNVIPATMSASFDFRVAPDVDFKAFEEQLQSWCQAAGEG
Sbjct: 241  PHLKEGSVTSVNLTKLEGGVAYNVIPATMSASFDFRVAPDVDFKAFEEQLQSWCQAAGEG 300

Query: 266  VTLEFAQKWMHPQVTPTDDSNPWWAAFSRVCKDMNLTLEPEIMPAATDNRYIRAVGVPAL 325
            VTLEFAQKWMHPQVTPTDDSNPWWAAFSRVCKDMNLTLEPEIMPAATDNRYIRAVGVPAL
Sbjct: 301  VTLEFAQKWMHPQVTPTDDSNPWWAAFSRVCKDMNLTLEPEIMPAATDNRYIRAVGVPAL 360

Query: 326  GFSPMNRTPVLLHDHDERLHEAVFLRGVDIYTRLLPALASVPALPSDS 373
            GFSPMNRTPVLLHDHDERLHEAVFLRGVDIYTRLLPALASVPALPSDS
Sbjct: 361  GFSPMNRTPVLLHDHDERLHEAVFLRGVDIYTRLLPALASVPALPSDS 408 (SEQ ID NO: 4)
```

Hmmer search results (Pfam):
Scores for sequence family classification (score includes all domains):

| Model | Description | Score | E-value | N |
|---|---|---|---|---|
| PF01546 | Peptidase family M20/M25/M40 | 282.2 | 6.7e-81 | 2 |

Parsed for domains:

| Model | Domain | seq-f | seq-t | hmm-f | hmm-t | score | E-value |
|---|---|---|---|---|---|---|---|
| PF01546 | 1/2 | 16 | 31 .. | 1 | 16 [. | 4.0 | 2.7 |
| PF01546 | 2/2 | 32 | 312 .. | 66 | 419 .] | 278.1 | 1.1e-79 |

FIGURE 2B

```
   1 GCTGCATGAC CACAGGGATT GGTGGGAAAT CCAGGGTCTG GACAGCCAAG
  51 CCAAGGAAGT CAGGAACCTA GAGGGTATGG GGAACGCGAT TTAACAATTA
 101 GCCAGCATTG GCCGGGCGCA GTGGCTCACA CCTGTAATCC CAGCACTTTG
 151 GGAGGCCGAG GCAGGCGGAT CACGAGGTCA GGAGATCGAG ACCATCCTGA
 201 CTAACACGGT GAAAACCCGT CTCTACTAAA AATACAAAAA ATTAGCCGAG
 251 CGTGGTGGCG GGTGACTTTA GTCCCAGCTA CTCAGTAGGC TGAGGCAGGA
 301 GAATGGTGTG AACCCGGGAG GCGGAGCTTG CAGTGAGCCA AGACCGAGAT
 351 CACACCACTG CACTCCACCC TGGGTGACAA AGCGAGTGAG ACTCCGTCTC
 401 AAAAAAAAAA AAAAAAAAA AAAAAAAAAA AAAAAAAAAA AAAAAAAACA
 451 TTAGCTGGGC ACTGTGGCTC ACATCTGTAA TCCCAGCACC TTGGGAGGCC
 501 AAGGCGGGTG GATCACCTGA GGTCAGGAGT TCAAGACCAC CCTGGCCAAC
 551 ATGACAAACC CTGTCTCTAC TAAAAATACA AAAATTAGCC CAGCGTGGTG
 601 GCACGCACCT GTAATCCCAG CTACTCTGGA GGCTGAGGCA GGAGAATCAC
 651 TTGAACCCAG GAGGCGGAGT TTTCAGCGAG CCGAGAAGGA GCCACTGCAC
 701 TCCAGCCTGG GCAGCAGAGT GAGACTCCAT CTCAAAAAAA TAAATAGCTA
 751 AATAATTAGC CAGCATTGTT ATGAGTTAAA GTCTATTTGC CCGCATGAAT
 801 AAATAGGTAA ATAATTAGCC AGCATTGTTG TGAGTTAAAA TCTATTTGCC
 851 CGCATGACAG AGTGAGACTC TGTATCAAAA AATAACTAA ATAAAGAATT
 901 ATCCAGCATT GTTATGAGTT AAAGTCCATT TGCCCCCATG TTATGTGTGA
 951 GCAGCCAAGA CTTAAACCTC AGGAAAGGTG GGACAGAACC CTTCCCACAG
1001 CGTGCCTCCT TGGCCTAGAG ATTGAAGTCT TTGTCCCTCA CCCTTCCCCA
1051 AGCTGACTCA GCCCCTGGAG CAGAGGGCAG ACCTGGCTGG GAGTACAAAG
1101 GGCAGCTGGG GCACAAGTGG GCAACTGCAG CTGTGGCCTG CAGGGGGCCA
1151 GTGGTACACC TGTGCCTGTT TAGCCTCCCC CTCTGGTGGC TGCAGAAGAG
1201 CCAGTTTCCT CACACTGTCC ATCCAGGGTC ACAATTACAT CCATTCACAG
1251 TGACTTCATC ACACCCACCC ACCATCTCAC ACTGTCACAT ACACAATCAT
1301 ATCCACTGAT AGACTGCACA CGCAGTGGCA CGCTTAAACC GTCACACGTG
1351 CTCTTGTCCA TGCATTCATT CCCATTCTAG GCACTGTCCG GGCTCGGCAC
1401 GGCCCCGGGC AGAACCTTGC AGGAAGTGGA GCTCACAGCC TCCTGGAGTT
1451 CAGTGTGGGC AGACAGACAT TGGCCAATAA CTTCAGTACA AGTGGAGCTG
1501 AGGCGTCAGG GAGGACCTCC CCGAGGGGCT GAGGCCTGCA GTGGGGAGCC
1551 GTTGGAGACT TGCCGAGGAG GGCGAGGGCG CAGGCCCAGG GCTTTGCAGC
1601 TCTGCATCTT GAGAGCCTCG GGGCGGCCCC CTTTCCTCCC GCCCTATCCG
1651 GGGGCTGAAG GAGGAGGCGC CCTTAGGGGA CGGGACCGTC CTGAGCTCCC
1701 GGCGCATACC TGGGGCAGG AGTGGCAGGC GTGTCGTGTG GGGCGGGGCG
1751 AGCCTGTCAG AGCAGGGCCA GCCCGGAGCT CGCAACTCGC GGGGCGGCGC
1801 TGGCCGCGGC GGCCGCTGCC CGGGACGGG ATCCGGATCT AATCCTCCAG
1851 TAATCTCGCT GAGGCCCGAA CCAGAGGCGG GCGGGGACAT CCGCGCCGAC
1901 GCGGCCGCTG GCGCCGGGAC GGCCCTCACT GACGGTCTTC GGTCTCCGCC
1951 CCGACATCCG GCCTCGGCCA CGTGGTGGGC GGACCGGGGC GGTCGTGAGC
2001 CTGCGACCTC GCAGGCGACC TCGCTGGACC CTAAGTCCAG GCCACAGTCA
2051 GGGAAGGGCG CTGAGAGGCG AGCGTGAGCC CAGCGACAGG AGAGTGAGGT
2101 GGGGGCCCTG GGGAGGGATA GAGGGACTGG GGCTCCGTGG CTTGAAAGCC
2151 GGGCAACTGG GAGGCGTTGG GGTTTTTCTT GTTTGTTTTT TGTTTTTGTT
2201 TTTGCCTTTT TTTTTTTTTA GGAGGGCGGG GGGAGTACAA GTCTGGGTTC
2251 AAACCTTGCT CAGCTACTCT ATGAGCTGTC CTTGAACCTC TCTGAGCCTC
2301 TCAGCTTTCT CCTCTGTAAA GTGGGCATTC TGAGCACAAA CTTCATGGGG
2351 CTCTTTTGGG GATTAAATAA GGAAATGTGC TGGAAGCAGA CAGCCCAGCG
2401 CCTGAAACAG AATGGGTGCT CCTTAATGGG GGCTCCGAAA CACGGTATCC
2451 TACCCCTGTG GGAAGTCCGG GAGCCGCCGT GGGGACAGGC TGTGTGCAGG
2501 AGCTCACCAT TTCCAGGGTC TTGGAGGGGT AGTTAGCCAT TCACTTTGCC
2551 CCCAGCTCAC CACGCGCAGC GCCATGACCA GCAAGGGTCC CGAGGAGGAG
2601 CACCCATCGG TGACGCTCTT CCGCCAGTAC CTGCGTATCC GCACTGTCCA
2651 GCCCAAGCCT GACTATGGTG AGAAGACGGT GGTTCCAGAG CCTGTGACGG
2701 GGCCTAAGGG ACGGGACTG TGCTCTAAAC CAGCCTCCAA CCCCTGTCCA
2751 CCAGCTGAGC CCCACTCTGC TGTCCCAAAT GGCTCCCCAA CCCCTCCAGC
2801 CATTCCCCAA GTAAATAGAC TGAGGCAGCC CCTCCAGGTT AGGGAGGAAC
2851 CCTTTCCCCA GAGACTCTGC TGCTGACCAA GGTTACTCCT GGCAGCTGGT
2901 TAAAGAAAAA CTTCACCTCA CTCTCCAGGG CAGGAGTGGT GGGGAAGCC
2951 TGAGGCAGCC ACAGGGAAAG GAGAGGCCCT CCAGAAGCCC ACTGGGGCTG
3001 GACAAAGGCC ACAGCCCTTA GGGAGTCAAG CTTGGTGGCT AGGGCCTGGG
3051 AGGTGGCTCC TGCCTGTTAT CCCAGCACTT CAGGAGGTTG AGGCTGGCAG
3101 ATTGCTTGGG CCCAGGAGTT CAAGACTAGC TTGAGCAACA TGGCAAGACT
3151 CTGTCTCTAC AGAAAAAATA CAAAAATTAG TCAGGAATGG TGGCACACCT
3201 GTAGTCCCAG CTACTCCAGA GGTTGAGGTG GGAGGATCGC TTGAGCCTGG
```

FIGURE 3A

```
3251 GAGGTTGAGG CTGCAGTGAG CCGAGATCGC ACCACTTCAC TCCTGCCTTG
3301 GTGACAGAGT GAGACCCTGT CTCAAAAAAA AAAAAAAAAA AAGGAAAAGA
3351 AAAAAAAAAA ACTTAGTGGC TGGGAATTGT GTACATGGGT CCAAATTCCT
3401 CCTCTGTGAT TAATCAGCTG AGAGATGGTG GGTGAATCTC TTCATGTCTC
3451 TGTGCCATAG TTTCCCATAT TTAAGGAAGA TAACACCTTC CTCCAACCCT
3501 GTGTCCAGAC ATCCCCCTGG ACTTCCAGAA AGGGTCACTG AGTAGCCAAA
3551 AATATCTTCT TTCTTGGGGA TGGAAATGCA AGCATCTCTG AGGGATATGG
3601 AGTGTGTCGG GGAGGCAGCA GCCCATTTCT GGGTATGCTC CACTCTCCGG
3651 GCTGCCTGGG CTGGTGGGAA GCTGTGGGTA GGCAGAAGCA GCCCCAAGAC
3701 ACTCTGTGCC TCCAGGAGCT GCTGTGGCTT TCTTTGAGGA GACAGCCCGC
3751 CAGCTGGGCC TGGGCTGTCA GAAAGTAGAG GTGAGCCTGG GGCCCTAAGC
3801 GGGGAAGGGA GGTGGGCCTG GGCACTTCCT CACCCTGCTC AGACCACCTA
3851 CCCTCCTGAC CATCTCCAGG TGCACCTGG CTATGTGGTG ACCGTGTTGA
3901 CCTGGCCAGG CACCAACCCT ACACTCTCCT CCATCTTGCT CAACTCCCAC
3951 ACGGATGTGG TGCCTGTCTT CAAGGTGTGT AAGGGGCTGG GGAGGTGGGC
4001 AGTGCAGGCC TTGGGGACAG ACATGATGCA GACCCCAGGA TTCAACCTCA
4051 AGTTGCTCAT GGTCCTGGCC CCAGTCCTGA CACTAACTCT CAACATCCTT
4101 ATGACATTAC ACCACTCAAG CAGCCTTCAT CCAGCAGCAA GTTCTGGGCC
4151 AGAGTGGGGT GGGGACTGGG GGGTGGGAAG CAGGAGACAG CAATGGGGGA
4201 TGGCAATCAG CTGCCTTCTT CAGCCCCCGT CTTTCCTCTC CCACCACTCC
4251 ACCTGTCACT CCAACCCTAT GGTGGGCTCC TAGGGCAGGG CCACTGTTGA
4301 CCAGAGTGGA TTAATGGCTA AATTTGGGGT TTGGGCCCCT CTTCCCATCC
4351 CTGCCCCCAG GAACATTGGA GTCACGACCC CTTTGAGGCC TTCAAGGATT
4401 CTGAGGGCTA CATCTATGCC AGGGGTGCCC AGGACATGAA GTGCGTCAGC
4451 ATCCAGTGAG TGTCCTCCAT TCCTACTCCT CCACAATGTC CCCACTGGTC
4501 CAGTGGATTG AAGCAGGACC TGAGGGGGTG ATTGGAGAAA CTCAAGGCCA
4551 AGGAACACCG TGACCTCTTG GACAGGAACT ACTGCCATGA CCATTGCATG
4601 GATAGGGAGA TTCAGACCAG AGAGGGGCAG GGACTTTCTG GAGTCCCTAT
4651 CAGGGTGTGG CAGGGTAAAG TCCAGGACAC AGGACTCCAG CCTGCTGGCC
4701 CTGCCTGTGG GGCCAGCCTG CGCATCTGGT GGCTCCCCCA GCACCTGGCT
4751 TATGCCCCCT CAGGTACCTG GAAGCTGTGA GGAGGCTGAA GGTGGAGGGC
4801 CACCGGTTCC CCAGAACCAT CCACATGACC TTTGTGCCTG GTAGGAGTGG
4851 CTCAGATACC TTTGGGAAAG GGGAGGGTGG GGCGGGGCAG CCTCCTCATC
4901 TCACGTCCCT GCTGCTTTTA CAGATGAGGA GGTTGGGGGT CACCAAGGCA
4951 TGGAGCTGTT CGTGCAGCGG CCTGAGTTCC ACGCCCTGAG GGCAGGCTTT
5001 GCCCTGGATG AGGGTGAGCA GGTTGGCAAG CCAATGAGCA GCCAGGCAGG
5051 GAGTAGGAGG CTGCTAGTGG GGACTGAGCT GCTCCACCCT CTGAACCCCC
5101 TTTCCCTCCT CAGGCATAGC CAATCCCACT GATGCCTTCA CTGTCTTTTA
5151 TAGTGAGCGG AGTCCCTGGT GTAAGTATGA GCTTGGAGGG AGGGCTCACT
5201 CTACAGGCGG GAGGCTAGGC CAGAAAGGGC ACGGTCCTAT GCAGGGTTGC
5251 ACAGCAAAGT TGAGGCCTGA GAAGGCCTTG AACCCAGGGC CTCTACCTCC
5301 CAGCTCTTTC CTATCTGAGC TTCTCTGAGG GCAAGCCCTG AATGGGACAGA
5351 AACCAGCTGT ATGCTACGGG CCCTGAGTGG GGACAGGACC CTGCCAGAGG
5401 AGCCTGGAAT GAGGGGGAGA CCTGGGCCCA CCCCAGGCTG ATTGTGTCTC
5451 CAGCCCCTCA GGCTGAAGAC ACTGCCTTCC CCCTACACCT CCCCAGGGGT
5501 GCGGGTTACC AGCACTGGGA GGCAGGCCA TGCCTCACGC TTCATGGAGG
5551 ACACAGCAGC AGAGAAGCTG GTACGTGGCA CCCCAGGAGG GAGTCTGGGA
5601 GTTCAGGAGG CTCTATCCTG AGGCCACTGT CCCATTTAAC CTCATATTCT
5651 CATAGCACAA GGTTGTAAAC TCCATCCTGG CATTCCGGGA GAAGGAATGG
5701 CAGAGGTGAG GCAGCCTGGG AGGCAGTGGG GTGGCTCTGG GAGGCGGTAC
5751 CACAGAGGAT AGAGTCTGAG CCACCTCTTT TATCTGTTGC TGCCGCTACC
5801 CTGCCCCCAC ACCACAGGCT GCAGTCAAAC CCCCACCTGA AAGAGGGGTC
5851 CGTGACCTCC GTGAACCTGA CTAAGCTAGA GGGTGGCGTG GCCTATAACG
5901 TGATACCTGC CACCATGAGC GCCAGCTTTG ACTTCCGTGT GGCACCGGAT
5951 GTGGACTTCA AGGTGCCACC TCCACCTGGG TTTGGAGGAG GGATCCTGGG
6001 TCCTCAGTCT TGTCCTAGAG GCCTCTGGAA AGCCTGAAGG ATCAGCTCGT
6051 CTCCCTTCTC TTAGGCTTTT GAGGAGCAGC TGCAGAGCTG GTGCCAGGCA
6101 GCTGGCGAGG GGGTCACCCT AGAGTTTGCT CAGGTATGGA CTTGGGACAT
6151 GTGATGGGAG AGTGTGGGAG CCGGGGGAGA CCCAAGTGTG CAACAGTGGA
6201 GTGTGTGCTT GGTGTGTCTG CATATGTCTG GGCATTTCTT TATCTGTGAC
6251 AGACACATTT TATTCCAACA AGCATTCATT GTAGAGGCCA CTGTGGGTGC
6301 TGGGGAATGC TGTGGGGAGT AAAATTAGGC ACAGTTCATG CCCTTGTATG
6351 GTGAAACGGG GAGATATAAA TCAAACATTT ATGTGATATT ACTTTTTTCT
6401 GAGAGAATCT CACTCCGTCA CCCAGGCTGC AGTGCAGTGG CACAATCTCG
6451 GCTCACCTCC GCCTCCCGGG TTCAAGCAAT TCTTGTGCCT CAGCCTCCAG
```

FIGURE 3B

```
6501 AGTAGTTGGG ATTACAGGCA CCTGCCACCA CGCCCAGCTA ATTTTTGCAT
6551 TTTTAGTAGA GACAGTGTTT CACCATGTTG GCCAGGCTTG TCTCGAACTC
6601 CTGGCCTCAA GTGATCCACC CACCTTGGCC TCGCAAAATG CTGGGATTAC
6651 AGGCATGAGC CACTGCGCCC AGCCGTACTT TCATATAACC CATGTGGTAC
6701 AGGAAAGGGT GGCCCCTTGC ACTCTGAAAA CCTGTAACTG GAGTATCCAA
6751 CTAGTCTGAG AGGTCTGGGG GAGCCATCTT GAGGAAGGGG CACTTGGGCT
6801 AGGATCTGAA GGATGGACAG GAGGTAAGTA GACGGAGGGT GGGAAGGTCC
6851 CAGACCTAGG ACATTTGAGG GGCTGAAAGA GGACCTGTGG CTGGACTGGC
6901 TACCCAGATG TCTGGGTAGG TGAAGGAGTG GGGGTGGGGA GGTGTTATGT
6951 ACTAGGCACA GCCCACTCTA TGGGAAATAG GGCAAGATGC CCAGGCCCAT
7001 GTCCTGATCC TGCCATTCTT CCTGTCCCTC AGAAGTGGAT GCACCCCCAA
7051 GTGACACCTA CTGATGACTC AAACCCTTGG TGGGCAGCTT TTAGCCGGGT
7101 CTGCAAGGAT ATGTGAGCAC GCTGGCAGCC TCTCCTCACA GCCCAGCCCC
7151 CTACTCCTCT CCTTCCTGCT GCCCCCTCCC TTCTCCCTCC TTCTCCCACC
7201 TCTTTCCCAC CTTCCTTTGC CCCTTCAATT CTTCGCTTTC TCCCTCCCCA
7251 TTCATCAGGC TCTTTCTCCT ACAGGAACCT CACTCTGGAG CCTGAGATCA
7301 TGCCTGCTGC CACTGACAAC GGCTATATCC GCGCGGTGAG CCACTTGCAT
7351 ATAGTGCCTG GGCAGTGGAC TGGGCCTGAG TGCTGGCTTT TCCCTAACGG
7401 CTCTTCCTCA CCCCTGCAGG TGGGGGTCCC AGCTCTAGGC TTCTCACCCA
7451 TGAACCGCAC ACCTGTGCTG CTGCACGACC ACGATGAACG GCTGCATGAG
7501 GCTGTGTTCC TCCGTGGGGT GGACATATAT ACACGCCTGC TGCCTGCCCT
7551 TGCCAGTGTG CCTGCCCTGC CCAGTGCCTA CTGAGCCCTG GAACTCCTAA
7601 ACCTTTGCCC CTGGGGCTTC CATCCCAACC AGTGCCAAGG ACCTCCTCTT
7651 CCCCCTTCCA AATAATAAAG TCTATGGACA GGGCTGTCTC TGAAGTACTA
7701 ACACAAGGAC ACTCGTGGAG CAAGAATTTT CCTTTTCCTG GGGACATGTT
7751 ACCATCTCCA TTTCACAGAT GAGGAAACTG AGCCTGGCTG TTAGCACTTC
7801 CCCACTACCC CACACTGCTC TGTGCCCCTT GACACAGCAC ACCCATTCAG
7851 TACCATCCAG CCATGTCTGT GCCTAGCAAG AAAGGGCCAC AGTTCCTATT
7901 TGAGTGGCCA CCATACTTAG TTCTGACCTA TCAGGGATTC CATTCCCATT
7951 AAAGAGGGAT ACTAAGGACC TCAGGAACCA CTCCCATCTT CCTGGGTGTA
8001 CATCTGGGAT CCTGAGACAG TACCACAGCTG GGCCCCTGCT
8051 AGATGAGGGG CAGGCAGAGG GCCAACGGTG ACTGCTGGCT CCTGTCAAAA
8101 CCTGTACACC CTTGTGTTGG CAGCAGGGGC CACAGAGGGG CAGGGTCCCT
8151 GGTAGACTAG GTCAGTTCAT CTTAGAGGCC TCAGCACCCT GGATCTGTGT
8201 GTGCAGAGGC CCAGGAACTG GGCTTTCATC TCAGCCTTGC TAGGACCCCC
8251 AGGTAGTACC AAGAGTAAAC TATGGCCCCA GTAGCAGAGC CTGATCTAGC
8301 CAGATCTGCT CTATCCTGTT CTGACTTCCC TGAGCATGGG GCAGGAGAGA
8351 CAGGGCTGGG GTGGGATAGT TGGATTTTTT AAGTTTCTAG TTGTAGCCAG
8401 AAGTCCAGAG CCTGGCTCTG GGCTGCAGGC TTAGTACTAA TAGAAATAAC
8451 AATCACTCCT GCTCACAGTT GACAGACTTGA CTGGCTTTTT
8501 TTTTTTTTTT TTTTTTTTGA GATGGAGTCT TTCTCTGTCG CCCAGGCTGG
8551 CGTGCAGTGG CGCGATCTCG GCTCACTGCA AACTCCGCTT CCTGGGTTCA
8601 CGCCATTCTC CTGCCTCAGT TTCCTGAGTA GTTGGGACTA CAGGCCCCCG
8651 CCACCACGCC CAGCTTTTTG TATTTTTAGT AGAGACGGGG TTTCACCTCC
8701 GCCTCCCAGG TTCAAGGGAT TCTCCTGCCT CAGCCTCCCA AGTAGCTGGG
8751 ACTACATGCG CGTGCCACCA CGGCCGGCTA ATTTTTGTAT TTTTAGTAGA
8801 GACGGTTTCA CCACGTTGAA CAGGATGATT TCGATCTCTT GACCTCAGGG
8851 GATCCGCCTG CCTCGGCCTC CCAAAGTGCT GGTGAGAGGT GACAGCGTGC
8901 TGGCAGTCCT CACAGCCCTC GCTCGCTCTC CCCGCCTCCT CTGCCTCGGC
8951 TCCCACTTTG GTGGCACTTG AGGAGCCCTT CAGCCCACCG CTGCACTGTA
9001 GGAACCCCTT TCTGGGCTGG CCAAGGCCAG AGCCGGCTCC CTCAGTTCGC
9051 AGGGAGGTGT GGAGGGAGAG GCGCGAGCGG GAACCGGGGC TGCCCGCCGC
9101 GCTTGCGGGC CAGCTGGAGT TCCGGGTGGG CGTGGGTTTG GCGGGCCCCG
9151 CACTCGCACT CGGAGCAGCC GGCCGCCCT GCCGTCCCCG CCGTCCCCGG
9201 GCAATGAGGG GCTTAGCACC CGGGCCAGTG GCTGCGGAGG GTGTACTGGG
9251 TCCCCCAGCA GTGCCAGGCC ACCGGCGCTG CTCTCGATTT CTCACCGGGT
9301 CTTAGCTGCC TTCCCGCGGG TCAGGGTTTG GGACCTGCAG CCCACCATGC
9351 CTTGAGCCCT CCCACCCCCT CCACTGGCTC CCGTGCGGCC CCAGCCTCCC
9401 CCATGAGCGC CGCCCCCCGC TCCACGGCAC CCAGTCCCAT CCACCACCCA
9451 AGGGCTGAGG AGTGCGGGCT CACGGAGCAG GACTGGCAGG CAGCTCCACC
9501 TGCAGCCCCG GTGCGGGATC CACTGGGTGA AGCCAGCTGG GCTCCTGAGT
9551 CTGGTGGGGA CGTGGAGAAC CTTTATGTCT AGCTCAGGGA TTGTAAATAC
9601 ACCAATCGGC ATTCTGTATC TAGCTCAAGG TTTGTAAACA CACCAATCAG
9651 CACCCTGTGT CTAGCTCAGG GTTTGTGAAT ACACCAATGG ACACTCTGTA
9701 TCTA (SEQ ID NO: 3)
```

FIGURE 3C

```
FEATURES:
Start:    2574
Exon:     2574-2667
Intron:   2668-3909
Exon:     3910-3974
Intron:   3975-4360
Exon:     4361-4455
Intron:   4456-4763
Exon:     4764-4840
Intron:   4841-4923
Exon:     4924-5013
Intron:   5014-5113
Exon:     5114-5170
Intron:   5171-5496
Exon:     5497-5570
Intron:   5571-5655
Exon:     5656-5705
Intron:   5706-5817
Exon:     5818-5962
Intron:   5963-6064
Exon:     6065-6133
Intron:   6134-7032
Exon:     7033-7112
Intron:   7113-7274
Exon:     7275-7335
Intron:   7336-7419
Exon:     7420-7581
Stop:     7582
```

SNPs:

| DNA Position | Major | Minor | Domain | Protein Position | Major | Minor |
|---|---|---|---|---|---|---|
| 830 | A | G | Beyond ORF(5') | | | |
| 2829 | T | C | Intron | | | |
| 4512 | C | A | Intron | | | |
| 4556 | C | T | Intron | | | |
| 4904 | C | T | Intron | | | |
| 5284 | C | T | Intron | | | |
| 5585 | A | G | Intron | | | |
| 5809 | G | A | Intron | | | |
| 7585 | G | C | Beyond ORF(3') | | | |
| 8366 | G | A | Beyond ORF(3') | | | |

Context:

DNA
Position

830    TTCAAGACCACCCTGGCCAACATGACAAACCCTGTCTCTACTAAAAATACAAAAATTAGC
       CCAGCGTGGTGGCACGCACCTGTAATCCCAGCTACTCTGGAGGCTGAGGCAGGAGAATCA
       CTTGAACCCAGGAGGCGGAGTTTTCAGCGAGCCGAGAAGGAGCCACTGCACTCCAGCCTG
       GGCAGCAGAGTGAGACTCCATCTCAAAAAAATAAATAGCTAAATAATTAGCCAGCATTGT
       TATGAGTTAAAGTCTATTTGCCCCGCATGAATAAATAGGTAAATAATTAGCCAGCATTGTT
       [A,G]
       TGAGTTAAAATCTATTTGCCCCGCATGACAGAGTGAGACTCTGTATCAAAAAAATAACTAA
       ATAAAGAATTATCCAGCATTGTTATGAGTTAAAGTCCATTTGCCCCCATGTTATGTGTGA
       GCAGCCAAGACTTAAACCTCAGGAAAGGTGGGACAGAACCCTTCCCACAGCGTGCCTCCT
       TGGCCTAGAGATTGAAGTCTTTGTCCCTCACCCTTCCCCAAGCTGACTCAGCCCCTGGAG
       CAGAGGGCAGACCTGGCTGGGAGTACAAAGGGCAGCTGGGGCACAAGTGGGCAACTGCAG (SEQ ID NO: 5)

FIGURE 3D

2829    GTAGTTAGCCATTCACTTTGCCCCCAGCTCACCACGCGCAGCGCCATGACCAGCAAGGGT
        CCCGAGGAGGAGCACCCATCGGTGACGCTCTTCCGCCAGTACCTGCGTATCCGCACTGTC
        CAGCCCAAGCCTGACTATGGTGAGAAGACGGTGGTTCCAGAGCCTGTGACGGGGCCTAAG
        GGACGGGGACTGTGCTCTAAACCAGCCTCCAACCCCTGTCACCCAGCTGAGCCCCACTCT
        GCTGTCCCAAATGGCTCCCCAACCCCTCCAGCCATTCCCCAAGTAAATAGACTGAGGCAG
        [T,C]
        CCCTCCAGGTTAGGGAGGAACCCTTTCCCCAGAGACTCTGCTGCTGACCAAGGTTACTCC
        TGGCAGCTGGTTAAAGAAAAACTTCACCTCACTCTCCAGGGCAGGAGTGGTGGGGGAAGC
        CTGAGGCAGCCACAGGGAAAGGAGAGGCCCTCCAGAAGCCCACTGGGGCTGGACAAAGGC
        CACAGCCCTTAGGGAGTCAAGCTTGGTGGCTAGGGCCTGGGAGGTGGCTCCTGCCTGTTA
        TCCCAGCACTTCAGGAGGTTGAGGCTGGCAGATTGCTTGGGCCCAGGAGTTCAAGACTAG (SEQ ID NO: 6)

4512    TGCCTTCTTCAGCCCCCGTCTTTCCTCTCCCACCACTCCACCTGTCACTCCAACCCTATG
        GTGGGCTCCTAGGGCAGGGCCACTGTTGACCAGAGTGGATTAATGGCTAAATTTGGGGTT
        TGGGCCCCTCTTCCCATCCCTGCCCCCAGGAACATTGGAGTCACGACCCCTTTGAGGCCT
        TCAAGGATTCTGAGGGCTACATCTATGCCAGGGGTGCCCAGGACATGAAGTGCGTCAGCA
        TCCAGTGAGTGTCCTCCATTCCTACTCCTCCACAATGTCCCCACTGGTCCAGTGGATTGA
        [C,A]
        GCAGGACCTGAGGGGGTGATTGGAGAAACTCAAGGCCAAGGAACACCGTGACCTCTTGGA
        CAGGAACTACTGCCATGACCATTGCATGGATAGGGAGATTCAGACCAGAGAGGGGCAGGG
        ACTTTCTGGAGTCCCTATCAGGGTGTGGCAGGGTAAAGTCCAGGACACAGGACTCCAGCC
        TGCTGGCCCTGCCTGTGGGGCCAGCCTGCGCATCTGGTGGCTCCCCAGCACCTGGCTTA
        TGCCCCCTCAGGTACCTGGAAGCTGTGAGGAGGCTGAAGGTGGAGGGCCACCGGTTCCCC (SEQ ID NO: 7)

4556    TCACTCCAACCCTATGGTGGGCTCCTAGGGCAGGGCCACTGTTGACCAGAGTGGATTAAT
        GGCTAAATTTGGGGTTTGGGCCCCTCTTCCCATCCCTGCCCCCAGGAACATTGGAGTCAC
        GACCCCTTTGAGGCCTTCAAGGATTCTGAGGGCTACATCTATGCCAGGGGTGCCCAGGAC
        ATGAAGTGCGTCAGCATCCAGTGAGTGTCCTCCATTCCTACTCCTCCACAATGTCCCCAC
        TGGTCCAGTGGATTGAAGCAGGACCTGAGGGGGTGATTGGAGAAACTCAAGGCCAAGGAA
        [C,T]
        ACCGTGACCTCTTGGACAGGAACTACTGCCATGACCATTGCATGGATAGGGAGATTCAGA
        CCAGAGAGGGGCAGGGACTTTCTGGAGTCCCTATCAGGGTGTGGCAGGGTAAAGTCCAGG
        ACACAGGACTCCAGCCTGCTGGCCCTGCCTGTGGGGCCAGCCTGCGCATCTGGTGGCTCC
        CCAGCACCTGGCTTATGCCCCCTCAGGTACCTGGAAGCTGTGAGGAGGCTGAAGGTGGA
        GGGCCACCGGTTCCCCAGAACCATCCACATGACCTTTGTGCCTGGTAGGAGTGGCTCAGA (SEQ ID NO: 8)

4904    AGGGAGATTCAGACCAGAGAGGGGCAGGGACTTTCTGGAGTCCCTATCAGGGTGTGGCAG
        GGTAAAGTCCAGGACACAGGACTCCAGCCTGCTGGCCCTGCCTGTGGGGCCAGCCTGCGC
        ATCTGGTGGCTCCCCAGCACCTGGCTTATGCCCCCTCAGGTACCTGGAAGCTGTGAGGA
        GGCTGAAGGTGGAGGGCCACCGGTTCCCCAGAACCATCCACATGACCTTTGTGCCTGGTA
        GGAGTGGCTCAGATACCTTTGGGAAAGGGGAGGGTGGGCGGGGCAGCCTCCTCATCTCA
        [C,T]
        GTCCCTGCTGCTTTTACAGATGAGGAGGTTGGGGGTCACCAAGGCATGGAGCTGTTCGTG
        CAGCGGCCTGAGTTCCACGCCCTGAGGGCAGGCTTTGCCCTGGATGAGGGTGAGCAGGTT
        GGCAAGCCAATGAGCAGCCAGGCAGGGAGTAGGAGGCTGCTAGTGGGGACTGAGCTGCTC
        CACCCTCTGAACCCCCTTTCCCTCCTCAGGCATAGCCAATCCCACTGATGCCTTCACTGT
        CTTTTATAGTGAGCGGAGTCCCTGGTGTAAGTATGAGCTTGGAGGGAGGGCTCACTCTAC (SEQ ID NO: 9)

5284    CCCTGAGGGCAGGCTTTGCCCTGGATGAGGGTGAGCAGGTTGGCAAGCCAATGAGCAGCC
        AGGCAGGGAGTAGGAGGCTGCTAGTGGGGACTGAGCTGCTCCACCCTCTGAACCCCCTTT
        CCCTCCTCAGGCATAGCCAATCCCACTGATGCCTTCACTGTCTTTTATAGTGAGCGGAGT
        CCCTGGTGTAAGTATGAGCTTGGAGGGAGGGCTCACTCTACAGGCGGGAGGCTAGGCCAG
        AAAGGGCACGGTCCTATGCAGGGTTGCACAGCAAAGTTGAGGCCTGAGAAGGCCTTGAAC
        [C,T]
        CAGGGCCTCTACCTCCCAGCTCTTTCCTATCTGAGCTTCTCTGAGGGCAAGCCCTGAATG
        GGCAGAAACCAGCTGTATGCTACGGGCCCTGAGTGGGACAGGACCCTGCCAGAGGAGCC
        TGGAATGAGGGGGAGACCTGGGCCCACCCCAGGCTGATTGTGTCTCCAGCCCCTCAGGCT
        GAAGACACTGCCTTCCCCCTACACCTCCCCAGGGGTGCGGGTTACCAGCACTGGGAGGCC
        AGGCCATGCCTCACGCTTCATGGAGGACACAGCAGCAGAGAAGCTGGTACGTGGCACCCC (SEQ ID NO: 10)

5585    CAGGGCCTCTACCTCCCAGCTCTTTCCTATCTGAGCTTCTCTGAGGGCAAGCCCTGAATG
        GGCAGAAACCAGCTGTATGCTACGGGCCCTGAGTGGGACAGGACCCTGCCAGAGGAGCC
        TGGAATGAGGGGGAGACCTGGGCCCACCCCAGGCTGATTGTGTCTCCAGCCCCTCAGGCT
        GAAGACACTGCCTTCCCCCTACACCTCCCCAGGGGTGCGGGTTACCAGCACTGGGAGGCC
        AGGCCATGCCTCACGCTTCATGGAGGACACAGCAGCAGAGAAGCTGGTACGTGGCACCCC

FIGURE 3E

```
           [A,G]
           GGAGGGAGTCTGGGAGTTCAGGAGGCTCTATCCTGAGGCCACTGTCCCATTTAACCTCAT
           ATTCTCATAGCACAAGGTTGTAAACTCCATCCTGGCATTCCGGGAGAAGGAATGGCAGAG
           GTGAGGCAGCCTGGGAGGCAGTGGGGTGGCTCTGGGAGGCGGTACCACAGAGGATAGAGT
           CTGAGCCACCTCTTTTATCTGTTGCTGCCGCTACCCTGCCCCCACACCACAGGCTGCAGT
           CAAACCCCCACCTGAAAGAGGGGTCCGTGACCTCCGTGAACCTGACTAAGCTAGAGGGTG  (SEQ ID NO: 11)

5809       CCAGCACTGGGAGGCCAGGCCATGCCTCACGCTTCATGGAGGACACAGCAGCAGAGAAGC
           TGGTACGTGGCACCCCAGGAGGGAGTCTGGGAGTTCAGGAGGCTCTATCCTGAGGCCACT
           GTCCCATTTAACCTCATATTCTCATAGCACAAGGTTGTAAACTCCATCCTGGCATTCCGG
           GAGAAGGAATGGCAGAGGTGAGGCAGCCTGGGAGGCAGTGGGGTGGCTCTGGGAGGCGGT
           ACCACAGAGGATAGAGTCTGAGCCACCTCTTTTATCTGTTGCTGCCGCTACCCTGCCCCC
           [G,A]
           CACCACAGGCTGCAGTCAAACCCCCACCTGAAAGAGGGGTCCGTGACCTCCGTGAACCTG
           ACTAAGCTAGAGGGTGGCGTGGCCTATAACGTGATACCTGCCACCATGAGCGCCAGCTTT
           GACTTCCGTGTGTGGCACCGGATGTGGACTTCAAGGTGCCACCTCCACCTGGGTTTGGAGGA
           GGGATCCTGGGTCCTCAGTCTTGTCCTAGAGGCCTCTGGAAAGCCTGAAGGATCAGCTCG
           TCTCCCTTCTCTTAGGCTTTTGAGGAGCAGCTGCAGAGCTGGTGCCAGGCAGCTGGCGAG  (SEQ ID NO: 12)

7585       CTGGAGCCTGAGATCATGCCTGCTGCCACTGACAACCGCTATATCCGCGCGGTGAGCCAC
           TTGCATATAGTGCCTGGGCAGTGGACTGGGCCTGAGTGCTGGCTTTTCCCTAACGGCTCT
           TCCTCACCCCTGCAGGTGGGGGTCCCAGCTCTAGGCTTCTCACCCATGAACCGCACACCT
           GTGCTGCTGCACGACCACGATGAACGGCTGCATGAGGCTGTGTTCCTCCGTGGGGTGGAC
           ATATATACACGCCTGCTGCCCTGCCCTTGCCAGTGTGCCTGCCCTGCCCAGTGACAGCTGA
           [G,C]
           CCCTGGAACTCCTAAACCTTTGCCCCTGGGGCTTCCATCCCAACCAGTGCCAAGGACCTC
           CTCTTCCCCCTTCCAAATAATAAAGTCTATGGACAGGGCTGTCTCTGAAGTACTAACACA
           AGGACACTCGTGGAGCAAGAATTTTCCTTTTTCCTGGGGACATGTTACCATCTCCATTTCA
           CAGATGAGGAAACTGAGCCTGGCTGTTAGCACTTCCCCACTACCCCACACTGCTCTGTGC
           CCCTTGACACAGCACACCCATTCAGTACCATCCAGCCATGTCTGTGCCTAGCAAGAAAGG  (SEQ ID NO: 13)

8366       AGAGGGCCAACGGTGACTGCTGGCTCCTGTCAAAACCTGTACACCCTTGTGTTGGCAGCA
           GGGGCCACAGAGGGGCAGGGTCCCTGGTAGACTAGGTCAGTTCATCTTAGAGGCCTCAGC
           ACCCTGGATCTGTGTGTGCAGAGGCCAGGAACTGGGCTTTCATCTCAGCCTTGCTAGGA
           CCCCCAGGTAGTACCAAGAGTAAACTATGGCCCCAGTAGCAGAGCCTGATCTAGCCAGAT
           CTGCTCTATCCTGTTCTGACTTCCCTGAGCATGGGCAGGAGAGACAGGGCTGGGGTGGG
           [G,A]
           TAGTTGGATTTTTTAAGTTTCTAGTTGTAGCCAGAAGTCCAGAGCCTGGCTCTGGGCTGC
           AGGCTTAGTACTAATAGAAATAACAATCACTCCTGCTCACAGTTGACAAGGAGCCAGGAC
           TTGACTGGCTTTTTTTTTTTTTTTTTTTTTTTTGAGATGGAGTCTTTCTCTGTCGCCCAGG
           CTGGCGTGCAGTGGCGCGATCTCGGCTCACTGCAAACTCCGCTTCCTGGGTTCACGCCAT
           TCTCCTGCCTCAGTTTCCTGAGTAGTTGGGACTACAGGCCCCCGCCACCACGCCCAGCTT  (SEQ ID NO: 14)
```

Chromosome map:
Chromosome # 3

FIGURE 3F

SEQUENCE LISTING

<160> NUMBER OF SEQ ID NOS: 27

<210> SEQ ID NO 1
<211> LENGTH: 1445
<212> TYPE: DNA
<213> ORGANISM: Homo sapiens

<400> SEQUENCE: 1

```
ctgcgacctc gcaggcgacc tcgctggacc ctaagtccag gccacagtca gggaagggcg        60
ctgagaggcg agcgtgagcc cagcgacagg agagtgagct caccacgcgc agcgccatga       120
ccagcaaggg tcccgaggag gagcacccat cggtgacgct cttccgccag tacctgcgta       180
tccgcactgt ccagcccaag cctgactatg gcaccaaccc tacactctcc tccatcttgc       240
tcaactccca cacggatgtg gtgcctgtct tcaaggaaca ttggagtcac gaccccttty       300
aggccttcaa ggattctgag ggctacatct atgccagggg tgcccaggac atgaagtgcg       360
tcagcatcca gtacctggaa gctgtgagga ggctgaaggt ggagggccac cggttcccca       420
gaaccatcca catgaccttt gtgcctgatg aggaggttgg gggtcaccaa ggcatggagc       480
tgttcgtgca gcggcctgag ttccacgccc tgagggcagg ctttgccctg gatgagggca       540
tagccaatcc cactgatgcc ttcactgtct tttatagtga gcggagtccc tggtgggtgc       600
gggttaccag cactgggagg ccaggccatg cctcacgctt catggaggac acagcagcag       660
agaagctgca caaggttgta aactccatcc tggcattccg ggagaaggaa tggcagaggc       720
tgcagtcaaa cccccacctg aaagaggggt ccgtgacctc cgtgaacctg actaagctag       780
agggtggcgt ggcctataac gtgatacctg ccaccatgag cgccagcttt gacttccgtg       840
tggcaccgga tgtggacttc aaggcttttg aggagcagct gcagagctgg tgccaggcag       900
ctggcgaggg ggtcacccta gagtttgctc agaagtggat gcaccccaa gtgacaccta       960 ctgatgactc aaaccctttgg tgggcagctt ttagccgggt ctgcaaggat atgaacctca      1020
ctctggagcc tgagatcatg cctgctgcca ctgacaaccg ctatatccgc gcggtgggg       1080 tcccagctct aggcttctca cccatgaacc gcacacctgt gctgctgcac gaccacgatg      1140
aacggctgca tgaggctgtg ttcctccgtg gggtggacat atatacacgc ctgctgcctg      1200
cccttgccag tgtgcctgcc ctgccagtg acagctgagc cctggaactc ctaaaccttt      1260 gccctgggg cttccatccc aaccagtgcc aaggacctcc tcttccccct tccaaataat      1320
aaagtctatg gacagggctg tctctgaagt actaacacaa aaaaaaaaaa aaaaaaaaaa      1380
```

```
aaaaaaaaaa aaaaaaaaaa aaaaaaaaaa aaaaaaaaaa aaaaaaaaaa aaaaaaaaaa    1440
aaaaa                                                                 1445

<210> SEQ ID NO 2
<211> LENGTH: 373
<212> TYPE: PRT
<213> ORGANISM: Homo sapiens

<400> SEQUENCE: 2

Met Thr Ser Lys Gly Pro Glu Glu His Pro Ser Val Thr Leu Phe
 1               5                  10                  15

Arg Gln Tyr Leu Arg Ile Arg Thr Val Gln Pro Lys Pro Asp Tyr Gly
                 20                  25                  30

Thr Asn Pro Thr Leu Ser Ser Ile Leu Leu Asn Ser His Thr Asp Val
             35                  40                  45

Val Pro Val Phe Lys Glu His Trp Ser His Asp Pro Phe Glu Ala Phe
 50                  55                  60

Lys Asp Ser Glu Gly Tyr Ile Tyr Ala Arg Gly Ala Gln Asp Met Lys
 65                  70                  75                  80

Cys Val Ser Ile Gln Tyr Leu Glu Ala Val Arg Arg Leu Lys Val Glu
                 85                  90                  95

Gly His Arg Phe Pro Arg Thr Ile His Met Thr Phe Val Pro Asp Glu
                100                 105                 110

Glu Val Gly Gly His Gln Gly Met Glu Leu Phe Val Gln Arg Pro Glu
            115                 120                 125

Phe His Ala Leu Arg Ala Gly Phe Ala Leu Asp Glu Gly Ile Ala Asn
130                 135                 140

Pro Thr Asp Ala Phe Thr Val Phe Tyr Ser Glu Arg Ser Pro Trp Trp
145                 150                 155                 160

Val Arg Val Thr Ser Thr Gly Arg Pro Gly His Ala Ser Arg Phe Met
                165                 170                 175

Glu Asp Thr Ala Ala Glu Lys Leu His Lys Val Val Asn Ser Ile Leu
            180                 185                 190

Ala Phe Arg Glu Lys Glu Trp Gln Arg Leu Gln Ser Asn Pro His Leu
        195                 200                 205

Lys Glu Gly Ser Val Thr Ser Val Asn Leu Thr Lys Leu Glu Gly Gly
210                 215                 220

Val Ala Tyr Asn Val Ile Pro Ala Thr Met Ser Ala Ser Phe Asp Phe
225                 230                 235                 240

Arg Val Ala Pro Asp Val Asp Phe Lys Ala Phe Glu Glu Gln Leu Gln
                245                 250                 255

Ser Trp Cys Gln Ala Ala Gly Glu Gly Val Thr Leu Glu Phe Ala Gln
            260                 265                 270

Lys Trp Met His Pro Gln Val Thr Pro Thr Asp Ser Asn Pro Trp
        275                 280                 285

Trp Ala Ala Phe Ser Arg Val Cys Lys Asp Met Asn Leu Thr Leu Glu
290                 295                 300

Pro Glu Ile Met Pro Ala Ala Thr Asp Asn Arg Tyr Ile Arg Ala Val
305                 310                 315                 320

Gly Val Pro Ala Leu Gly Phe Ser Pro Met Asn Arg Thr Pro Val Leu
                325                 330                 335

Leu His Asp His Asp Glu Arg Leu His Glu Ala Val Phe Leu Arg Gly
            340                 345                 350

Val Asp Ile Tyr Thr Arg Leu Leu Pro Ala Leu Ala Ser Val Pro Ala
```

| | | |
|---|---|---|
| 355 | 360 | 365 |

Leu Pro Ser Asp Ser
  370

<210> SEQ ID NO 3
<211> LENGTH: 9704
<212> TYPE: DNA
<213> ORGANISM: Homo sapiens

<400> SEQUENCE: 3

| | | | | | |
|---|---|---|---|---|---|
| gctgcatgac | cacagggatt | ggtgggaaat | ccagggtctg | acagccaag | ccaaggaagt | 60 |
| caggaaccta | gagggtatgg | ggaacgcgat | ttaacaatta | gccagcattg | gccgggcgca | 120 |
| gtggctcaca | cctgtaatcc | cagcactttg | ggaggccgag | gcaggcggat | cacgaggtca | 180 |
| ggagatcgag | accatcctga | ctaacacggt | gaaaacccgt | ctctactaaa | aatacaaaaa | 240 |
| attagccgag | cgtggtggcg | ggtgacttta | gtcccagcta | ctcagtaggc | tgaggcagga | 300 |
| gaatggtgtg | aacccgggag | gcggagcttg | cagtgagcca | agaccgagat | cacaccactg | 360 |
| cactccaccc | tgggtgacaa | agcgagtgag | actccgtctc | aaaaaaaaaa | aaaaaaaaa | 420 |
| aaaaaaaaa | aaaaaaaaa | aaaaaaaca | ttagctgggc | actgtggctc | acatctgtaa | 480 |
| tcccagcacc | ttgggaggcc | aaggcgggtg | gatcacctga | ggtcaggagt | tcaagaccac | 540 |
| cctggccaac | atgacaaacc | ctgtctctac | taaaaataca | aaaattagcc | cagcgtggtg | 600 |
| gcacgcacct | gtaatcccag | ctactctgga | ggctgaggca | ggagaatcac | ttgaacccag | 660 |
| gaggcggagt | tttcagcgag | ccgagaagga | gccactgcac | tccagcctgg | gcagcagagt | 720 |
| gagactccat | ctcaaaaaaa | taaatagcta | aataattagc | cagcattgtt | atgagttaaa | 780 |
| gtctatttgc | ccgcatgaat | aaataggtaa | ataattagcc | agcattgttg | tgagttaaaa | 840 |
| tctatttgcc | cgcatgacag | agtgagactc | tgtatcaaaa | aaataactaa | ataaagaatt | 900 |
| atccagcatt | gttatgagtt | aaagtccatt | gcccccatg | ttatgtgtga | gcagccaaga | 960 |
| cttaaacctc | aggaaaggtg | ggacagaacc | cttcccacag | cgtgcctcct | tggcctagag | 1020 |
| attgaagtct | ttgtccctca | cccttcccca | agctgactca | gccctggag | cagagggcag | 1080 |
| acctggctgg | gagtacaaag | ggcagctggg | gcacaagtgg | gcaactgcag | ctgtggcctg | 1140 |
| caggggggcca | gtggtacacc | tgtgcctgtt | tagcctcccc | ctctggtggc | tgcagaagag | 1200 |
| ccagtttcct | cacactgtcc | atccagggtc | acaattacat | ccattcacag | tgacttcatc | 1260 |
| acacccaccc | accatctcac | actgtcacat | acacaatcat | atccactgat | agactgcaca | 1320 |
| cgcagtggca | cgcttaaacc | gtcacacgtg | ctcttgtcca | tgcattcatt | cccattctag | 1380 |
| gcactgtccg | ggctcggcac | ggccccgggc | agaaccttgc | aggaagtgga | gctcacagcc | 1440 |
| tcctggagtt | cagtgtgggc | agacagacat | tggccaataa | cttcagtaca | agtggagctg | 1500 |
| aggcgtcagg | gaggacctcc | ccgaggggct | gaggcctgca | gtgggagcc | gttggagact | 1560 |
| tgccgaggag | ggcgagggcg | caggcccagg | gctttgcagc | tctgcatctt | gagagcctcg | 1620 |
| gggcggcccc | ctttcctccc | gcccctatccg | ggggctgaag | gaggaggcgc | ccttagggga | 1680 |
| cgggaccgtc | ctgagctccc | ggcgcatacc | tgggggcagg | agtggcaggc | gtgtcgtgtg | 1740 |
| gggcgggggcg | agcctgtcag | agcagggcca | gcccggagct | cgcaactcgc | ggggcggcgc | 1800 |
| tggccgcggc | ggccgctgcc | cggggacggg | atccggatct | aatcctccag | taatctcgct | 1860 |
| gaggcccgaa | ccagaggcgg | gcggggacat | ccgcgccgac | gcggccgctg | gcgccgggac | 1920 |
| ggccctcact | gacggtcttc | ggtctccgcc | ccgacatccg | gcctcggcca | cgtggtgggc | 1980 |

```
ggaccggggc ggtcctgagc ctgcgacctc gcaggcgacc tcgctggacc ctaagtccag    2040
gccacagtca gggaagggcg ctgagaggcg agcgtgagcc cagcgacagg agagtgaggt    2100
gggggccctg gggagggata gagggactgg ggctccgtgg cttgaaagcc gggcaactgg    2160
gaggcgttgg ggttttttctt gtttgttttt tgtttttgtt tttgccttttt tttttttttta    2220 ggagggcggg gggagtacaa gtctgggttc aaaccttgct cagctactct atgagctgtc    2280
cttgaacctc tctgagcctc tcagctttct cctctgtaaa gtgggcattc tgagcacaaa    2340
cttcatgggg ctcttttggg gattaaataa ggaaatgtgc tggaagcaga cagcccagcg    2400
cctgaaacag aatgggtgct ccttaatggg ggctccgaaa cacggtatcc tacccctgtg    2460
ggaagtccgg gagccgccgt ggggacaggc tgtgtgcagg agctcaccat ttccagggtc    2520 ttggagggggt agttagccat tcactttgcc cccagctcac cacgcgcagc gccatgacca    2580
gcaagggtcc cgaggaggag cacccatcgg tgacgctctt ccgccagtac ctgcgtatcc    2640
gcactgtcca gcccaagcct gactatggtg agaagacggt ggttccagag cctgtgacgg    2700
ggcctaaggg acggggactg tgctctaaac cagcctccaa cccctgtcac ccagctgagc    2760
cccactctgc tgtcccaaat ggctccccaa cccctccagc cattcccaa gtaaatagac    2820 tgaggcagcc cctccaggtt agggaggaac cctttcccca gagactctgc tgctgaccaa    2880
ggttactcct ggcagctggt taaagaaaaa cttcacctca ctctccaggg caggagtggt    2940
gggggaagcc tgaggcagcc acagggaaag gagaggccct ccagaagccc actggggctg    3000
gacaaaggcc acagcccttta gggagtcaag cttggtggct agggcctggg aggtggctcc    3060
tgcctgttat cccagcactt caggaggttg aggctggcag attgcttggg cccaggagtt    3120
caagactagc ttgagcaaca tggcaagact ctgtctctac agaaaaaata caaaaattag    3180
tcaggaatgg tggcacacct gtagtcccag ctactccaga ggttgaggtg gaggatcgc    3240 ttgagcctgg gaggttgagg ctgcagtgag ccgagatcgc accacttcac tcctgccttg    3300
gtgacagagt gagaccctgt ctcaaaaaa aaaaaaaaa aaggaaaaga aaaaaaaaa    3360 acttagtggc tgggaattgt gtacatgggt ccaaattcct cctctgtgat taatcagctg    3420
agagatggtg ggtgaatctc ttcatgtctc tgtgccatag tttcccatat ttaaggaaga    3480
taacaccttc ctccaaccct gtgtccagac atcccctgg acttccagaa agggtcactg    3540
agtagccaaa aatatcttct ttcttgggga tggaaatgca agcatctctg agggatatgg    3600
agtgtgtcgg ggaggcagca gcccatttct gggtatgctc cactctccgg gctgcctggg    3660
ctggtgggaa gctgtgggta ggcagaagca gccccaagac actctgtgcc tccaggagct    3720
gctgtggctt tctttgagga gacagcccgc cagctgggcc tgggctgtca gaaagtagag    3780
gtgagcctgg ggcctaagc ggggaaggga ggtgggcctg gcacttcct caccctgctc    3840 agaccaccta ccctcctgac catctccagg tggcacctgg ctatgtggtg accgtgttga    3900 cctgccagg caccaaccct acactctcct ccatcttgct caactcccac acggatgtgg    3960
tgcctgtctt caaggtgtgt aaggggctgg ggaggtgggc agtgcaggcc ttggggacag    4020
acatgatgca gaccccagga ttcaacctca agttgctcat ggtcctggcc ccagtcctga    4080
cactaactct caacatcctt atgacattac accactcaag cagccttcat ccagcagcaa    4140
gttctgggcc agagtgggt ggggactggg gggtgggaag caggagacag caatggggga    4200
tggcaatcag ctgccttctt cagcccccgt ctttcctctc ccaccactcc acctgtcact    4260 ccaacccctat ggtgggctcc tagggcaggg ccactgttga ccagagtgga ttaatggcta    4320
aatttggggt ttgggccct cttcccatcc ctgcccccag gaacattgga gtcacgaccc    4380
```

-continued

```
ctttgaggcc ttcaaggatt ctgagggcta catctatgcc aggggtgccc aggacatgaa    4440
gtgcgtcagc atccagtgag tgtcctccat tcctactcct ccacaatgtc cccactggtc    4500
cagtggattg aagcaggacc tgaggggtg attggagaaa ctcaaggcca aggaacaccg     4560
tgacctcttg acaggaact actgccatga ccattgcatg gatagggaga ttcagaccag     4620
agaggggcag ggactttctg gagtccctat cagggtgtgg cagggtaaag tccaggacac    4680
aggactccag cctgctggcc ctgcctgtgg ggccagcctg cgcatctggt ggctccccca    4740
gcacctggct tatgccccct caggtacctg aagctgtga ggaggctgaa ggtggagggc     4800
caccggttcc ccagaaccat ccacatgacc tttgtgcctg gtaggagtgg ctcagatacc    4860
tttgggaaag gggagggtgg ggcggggcag cctcctcatc tcacgtccct gctgctttta    4920
cagatgagga ggttgggggt caccaaggca tggagctgtt cgtgcagcgg cctgagttcc    4980
acgccctgag ggcaggcttt gccctggatg agggtgagca ggttggcaag ccaatgagca    5040
gccaggcagg gagtaggagg ctgctagtgg ggactgagct gctccaccct ctgaaccccc    5100 tttcctcct caggcatagc caatcccact gatgccttca ctgtcttta tagtgagcgg      5160 agtccctggt gtaagtatga gcttggaggg agggctcact ctacaggcgg gaggctaggc    5220
cagaaagggc acgtcctat gcagggttgc acagcaaagt tgaggcctga gaaggccttg     5280 aacccaggc ctctacctcc cagctctttc ctatctgagc ttctctgagg gcaagccctg     5340
aatgggcaga aaccagctgt atgctacggg ccctgagtgg ggacaggacc ctgccagagg    5400
agcctggaat gaggggggaga cctgggccca ccccaggctg attgtgtctc cagcccctca   5460
ggctgaagac actgccttcc ccctacacct ccccagggt gcgggttacc agcactggga    5520
ggccaggcca tgcctcacgc ttcatggagg acacagcagc agagaagctg gtacgtggca    5580
ccccaggagg gagtctggga gttcaggagg ctctatcctg aggccactgt cccatttaac    5640
ctcatattct catagcacaa ggttgtaaac tccatcctgg cattccggga gaaggaatgg    5700
cagaggtgag gcagcctggg aggcagtggg gtggctctgg gaggcggtac cacagaggat    5760
agagtctgag ccacctcttt tatctgttgc tgccgctacc ctgcccccac accacaggct    5820
gcagtcaaac ccccacctga agagggggtc cgtgacctcc gtgaacctga ctaagctaga    5880
gggtggcgtg gcctataacg tgatacctgc caccatgagc gccagctttg acttccgtgt    5940
ggcaccggat gtggacttca aggtgccacc tccacctggg tttggaggag ggatcctggg    6000
tcctcagtct tgtcctagag gcctctggaa agcctgaagg atcagctcgt ctcccttctc    6060
ttaggctttt gaggagcagc tgcagagctg gtgccaggca gctggcgagg gggtcaccct    6120
agagtttgct caggtatgga cttgggacat gtgatgggag agtgtgggag ccggggagaa    6180
cccaagtgtg caacagtgga gtgtgtgctt ggtgtgtctg catatgtctg ggcatttctt    6240
tatctgtgac agacacattt tattccaaca agcattcatt gtagaggcca ctgtgggtgc    6300
tggggaatgc tgtgggagt aaaattaggc acagttcatg cccttgtatg gtgaaacggg     6360
gagatataaa tcaaacattt atgtgatatt acttttttct gagagaatct cactccgtca    6420
cccaggctgc agtgcagtgg cacaatctcg gctcacctcc gcctcccggg ttcaagcaat    6480
tcttgtgcct cagcctccag agtagttggg attacaggca cctgccacca cgcccagcta    6540 attttttgcat ttttagtaga cagtgtttt caccatgttg gccaggcttg tctcgaactc    6600
ctggcctcaa gtgatccacc caccttggcc tcgcaaaatg ctgggattac aggcatgagc    6660
cactgcgccc agccgtactt tcatataacc catgtggtac aggaaagggt ggcccttgc    6720
```

```
actctgaaaa cctgtaactg gagtatccaa ctagtctgag aggtctgggg gagccatctt   6780
gaggaagggg cacttgggct aggatctgaa ggatggacag gaggtaagta gacggagggt   6840
gggaaggtcc cagacctagg acatttgagg ggctgaaaga ggacctgtgg ctggactggc   6900
tacccagatg tctgggtagg tgaaggagtg ggggtgggga ggtgttatgt actaggcaca   6960
gcccactcta tgggaaatag ggcaagatgc ccaggcccat gtcctgatcc tgccattctt   7020
cctgtccctc agaagtggat gcaccccaa gtgacaccta ctgatgactc aaacccttgg   7080
tgggcagctt ttagccgggt ctgcaaggat atgtgagcac gctggccagc tctcctcaca   7140
gcccagcccc ctactcctct ccttcctgct gcccctccc ttctccctcc ttctcccacc   7200
tctttcccac cttcctttgc cccttcaatt cttcgctttc tccctcccca ttcatcaggc   7260
tctttctcct acaggaacct cactctggag cctgagatca tgcctgctgc cactgacaac   7320
cgctatatcc gcgcggtgag ccacttgcat atagtgcctg gcagtggac tgggcctgag   7380
tgctggcttt tccctaacgg ctcttcctca cccctgcagg tggggtccc agctctaggc   7440
ttctcaccca tgaaccgcac acctgtgctg ctgcacgacc acgatgaacg gctgcatgag   7500
gctgtgttcc tccgtggggt ggacatatat acacgcctgc tgcctgccct tgccagtgtg   7560
cctgccctgc ccagtgacag ctgagccctg gaactcctaa acctttgccc ctgggcttc   7620
catcccaacc agtgccaagg acctcctctt cccccttcca aataataaag tctatggaca   7680
gggctgtctc tgaagtacta acacaaggac actcgtggag caagaatttt ccttttcctg   7740
gggacatgtt accatctcca tttcacagat gaggaaactg agcctggctg ttagcacttc   7800
cccactaccc cacactgctc tgtgcccctt gacacagcac acccattcag taccatccag   7860
ccatgtctgt gcctagcaag aaagggccac agttcctatt tgagtggcca ccatacttag   7920
ttctgaccta tcagggattc cattcccatt aaagagggat actaaggacc tcaggaacca   7980
ctcccatctt cctgggtgta catctgggat cctgagacag taccagaata gcaccagctg   8040
ggcccctgct agatgagggg caggcagagg gccaacggtg actgctggct cctgtcaaaa   8100
cctgtacacc cttgtgttgg cagcaggggc cacagagggg cagggtccct ggtagactag   8160
gtcagttcat cttagaggcc tcagcaccct ggatctgtgt gtgcagaggc caggaactg   8220
ggctttcatc tcagccttgc taggacccc aggtagtacc aagagtaaac tatgccccca   8280
gtagcagagc ctgatctagc cagatctgct ctatcctgtt ctgacttccc tgagcatggg   8340
gcaggagaga cagggctggg gtgggatagt tggattttt aagtttctag ttgtagccag   8400
aagtccagag cctggctctg ggctgcaggc ttagtactaa tagaaataac aatcactcct   8460
gctcacagtt gacaaggagc caggacttga ctggcttttt tttttttttt ttttttttga   8520
gatggagtct ttctctgtcg cccaggctgg cgtgcagtgg cgcgatctcg gctcactgca   8580
aactccgctt cctgggttca cgccattctc ctgcctcagt ttcctgagta gttgggacta   8640
caggcccccg ccaccacgcc cagcttttg tattttagt agagacgggg tttcacctcc   8700
gcctcccagg ttcaagggat tctcctgcct cagcctccca gtagctggg actacatgcg   8760
cgtgccacca cggccggcta attttgtat ttttagtaga cacggtttca ccacgttgaa   8820
caggatgatt tcgatctctt gacctcaggg gatccgcctg cctcggcctc ccaaagtgct   8880
ggtgagaggt gacagcgtgc tggcagtcct cacagccctc gctcgctctc ccgcctcct   8940
ctgcctcggc tcccacttg gtggcacttg aggagccctt cagcccaccg ctgcactgta   9000
ggaaccccctt tctgggctgg ccaaggccag agccggctcc ctcagttcgc agggaggtgt   9060
ggagggagag gcgcgagcgg gaaccggggc tgcccgccgc gcttgcgggc cagctggagt   9120
```

-continued

```
tccgggtggg cgtgggtttg gcgggccccg cactcgcact cggagcagcc ggccggccct    9180
gccgtccccg ccgtccccgg gcaatgaggg gcttagcacc cgggccagtg gctgcggagg    9240
gtgtactggg tcccccagca gtgccaggcc accggcgctg ctctcgattt ctcaccgggt    9300
cttagctgcc ttcccgcggg tcagggtttg ggacctgcag cccaccatgc cttgagccct    9360 cccacccct ccactggctc ccgtgcggcc ccagcctccc ccatgagcgc cgccccccgc     9420
tccacggcac ccagtcccat ccaccaccca agggctgagg agtgcgggct cacggagcag    9480
gactggcagg cagctccacc tgcagccccg gtgcgggatc cactgggtga agccagctgg    9540
gctcctgagt ctggtgggga cgtggagaac ctttatgtct agctcaggga ttgtaaatac    9600
accaatcggc attctgtatc tagctcaagg tttgtaaaca caccaatcag caccctgtgt    9660
ctagctcagg gtttgtgaat acaccaatgg acactctgta tcta                    9704
```

<210> SEQ ID NO 4
<211> LENGTH: 408
<212> TYPE: PRT
<213> ORGANISM: Homo sapiens

<400> SEQUENCE: 4

```
Met Thr Ser Lys Gly Pro Glu Glu His Pro Ser Val Thr Leu Phe
 1               5                  10                  15

Arg Gln Tyr Leu Arg Ile Arg Thr Val Gln Pro Lys Pro Asp Tyr Gly
            20                  25                  30

Ala Ala Val Ala Phe Phe Glu Thr Ala Arg Gln Leu Gly Leu Gly
            35                  40                  45

Cys Gln Lys Val Glu Val Ala Pro Gly Tyr Val Thr Val Leu Thr
        50                  55                  60

Trp Pro Gly Thr Asn Pro Thr Leu Ser Ser Ile Leu Leu Asn Ser His
65                  70                  75                  80

Thr Asp Val Val Pro Val Phe Lys Glu His Trp Ser His Asp Pro Phe
                85                  90                  95

Glu Ala Phe Lys Asp Ser Glu Gly Tyr Ile Tyr Ala Arg Gly Ala Gln
            100                 105                 110

Asp Met Lys Cys Val Ser Ile Gln Tyr Leu Glu Ala Val Arg Arg Leu
        115                 120                 125

Lys Val Glu Gly His Arg Phe Pro Arg Thr Ile His Met Thr Phe Val
    130                 135                 140

Pro Asp Glu Glu Val Gly Gly His Gln Gly Met Glu Leu Phe Val Gln
145                 150                 155                 160

Arg Pro Glu Phe His Ala Leu Arg Ala Gly Phe Ala Leu Asp Glu Gly
                165                 170                 175

Ile Ala Asn Pro Thr Asp Ala Phe Thr Val Phe Tyr Ser Glu Arg Ser
            180                 185                 190

Pro Trp Trp Val Arg Val Thr Ser Thr Gly Arg Pro Gly His Ala Ser
        195                 200                 205

Arg Phe Met Glu Asp Thr Ala Ala Glu Lys Leu His Lys Val Val Asn
    210                 215                 220

Ser Ile Leu Ala Phe Arg Glu Lys Glu Trp Gln Arg Leu Gln Ser Asn
225                 230                 235                 240

Pro His Leu Lys Glu Gly Ser Val Thr Ser Val Asn Leu Thr Lys Leu
                245                 250                 255

Glu Gly Gly Val Ala Tyr Asn Val Ile Pro Ala Thr Met Ser Ala Ser
            260                 265                 270
```

```
Phe Asp Phe Arg Val Ala Pro Asp Val Asp Phe Lys Ala Phe Glu Glu
            275                 280                 285

Gln Leu Gln Ser Trp Cys Gln Ala Ala Gly Glu Gly Val Thr Leu Glu
        290                 295                 300

Phe Ala Gln Lys Trp Met His Pro Gln Val Thr Pro Thr Asp Asp Ser
305                 310                 315                 320

Asn Pro Trp Trp Ala Ala Phe Ser Arg Val Cys Lys Asp Met Asn Leu
                325                 330                 335

Thr Leu Glu Pro Glu Ile Met Pro Ala Ala Thr Asp Asn Arg Tyr Ile
            340                 345                 350

Arg Ala Val Gly Val Pro Ala Leu Gly Phe Ser Pro Met Asn Arg Thr
        355                 360                 365

Pro Val Leu Leu His Asp His Asp Glu Arg Leu His Glu Ala Val Phe
    370                 375                 380

Leu Arg Gly Val Asp Ile Tyr Thr Arg Leu Leu Pro Ala Leu Ala Ser
385                 390                 395                 400

Val Pro Ala Leu Pro Ser Asp Ser
                405

<210> SEQ ID NO 5
<211> LENGTH: 601
<212> TYPE: DNA
<213> ORGANISM: Homo sapiens

<400> SEQUENCE: 5
ttcaagacca ccctggccaa catgacaaac cctgtctcta ctaaaaatac aaaaattagc    60
ccagcgtggt ggcacgcacc tgtaatccca gctactctgg aggctgaggc aggagaatca   120
cttgaaccca ggaggcggag ttttcagcga gccgagaagg agccactgca ctccagcctg   180
ggcagcagag tgagactcca tctcaaaaaa ataaatagct aaataattag ccagcattgt   240
tatgagttaa agtctatttg cccgcatgaa taaataggta ataattagc cagcattgtt   300 rtgagttaaa atctatttgc ccgcatgaca gagtgagact ctgtatcaaa aaataacta   360 aataaagaat tatccagcat tgttatgagt taaagtccat ttgcccccat gttatgtgtg   420
agcagccaag acttaaacct caggaaaggt gggacagaac ccttcccaca gcgtgcctcc   480
ttggcctaga gattgaagtc tttgtccctc acccttcccc aagctgactc agcccctgga   540
gcagagggca gacctggctg ggagtacaaa gggcagctgg gcacaagtg gcaactgca    600 g                                                                  601

<210> SEQ ID NO 6
<211> LENGTH: 601
<212> TYPE: DNA
<213> ORGANISM: Homo sapiens

<400> SEQUENCE: 6
gtagttagcc attcactttg cccccagctc accacgcgca gcgccatgac cagcaagggt    60
cccgaggagg agcacccatc ggtgacgctc ttccgccagt acctgcgtat ccgcactgtc   120
cagcccaagc ctgactatgg tgagaagacg gtggttccag agcctgtgac ggggcctaag   180
ggacggggac tgtgctctaa accagcctcc aaccctgtc acccagctga gccccactct    240
gctgtcccaa atggctcccc aaccctcca gccattcccc aagtaaatag actgaggcag   300 ycctcagg ttagggagga acccttccc cagagactct gctgctgacc aaggttactc    360
ctggcagctg gttaaagaaa aacttcacct cactctccag ggcaggagtg gtgggggaag   420
```

```
cctgaggcag ccacagggaa aggagaggcc ctccagaagc ccactggggc tggacaaagg    480
ccacagccct tagggagtca agcttggtgg ctagggcctg ggaggtggct cctgcctgtt    540
atcccagcac ttcaggaggt tgaggctggc agattgcttg ggcccaggag ttcaagacta    600
g                                                                    601

<210> SEQ ID NO 7
<211> LENGTH: 601
<212> TYPE: DNA
<213> ORGANISM: Homo sapiens

<400> SEQUENCE: 7
tgccttcttc agccccgtc tttcctctcc caccactcca cctgtcactc caaccctatg     60
gtgggctcct agggcagggc cactgttgac cagagtggat taatggctaa atttggggtt   120
tgggcccctc ttcccatccc tgccccagg aacattggag tcacgacccc tttgaggcct    180
tcaaggattc tgagggctac atctatgcca ggggtgccca ggacatgaag tgcgtcagca   240
tccagtgagt gtcctccatt cctactcctc acaatgtcc ccactggtcc agtggattga    300
mgcaggacct gagggggtga ttggagaaac tcaaggccaa ggaacaccgt gacctcttgg   360
acaggaacta ctgccatgac cattgcatgg atagggagat tcagaccaga gaggggcagg   420
gactttctgg agtccctatc agggtgtggc agggtaaagt ccaggacaca ggactccagc   480
ctgctggccc tgcctgtggg gccagcctgc gcatctggtg ctcccccag cacctggctt    540 atgccccctc aggtacctgg aagctgtgag gaggctgaag gtggagggcc accggttccc   600
c                                                                    601

<210> SEQ ID NO 8
<211> LENGTH: 601
<212> TYPE: DNA
<213> ORGANISM: Homo sapiens

<400> SEQUENCE: 8
tcactccaac cctatggtgg gctcctaggg cagggccact gttgaccaga gtggattaat     60
ggctaaattt ggggtttggg ccctcttcc catccctgcc cccaggaaca ttggagtcac    120 gaccccttg aggccttcaa ggattctgag gctacatct atgccagggg tgcccaggac     180
atgaagtgcg tcagcatcca gtgagtgtcc tcattccta ctcctccaca atgtccccac    240
tggtccagtg gattgaagca ggacctgagg gggtgattgg agaaactcaa ggccaaggaa   300
yaccgtgacc tcttggacag gaactactgc catgaccatt gcatggatag ggagattcag   360
accagagagg ggcagggact ttctggagtc cctatcaggg tgtggcaggg taaagtccag   420
gacacaggac tccagcctgc tggccctgcc tgtggggcca gcctgcgcat ctggtggctc   480
ccccagcacc tggcttatgc cccctcaggt acctggaagc tgtgaggagg ctgaaggtgg   540
agggccaccg gttccccaga accatccaca tgacctttgt gcctggtagg agtggctcag   600
a                                                                    601

<210> SEQ ID NO 9
<211> LENGTH: 601
<212> TYPE: DNA
<213> ORGANISM: Homo sapiens

<400> SEQUENCE: 9
agggagattc agaccagaga ggggcaggga ctttctggag tccctatcag ggtgtggcag    60
```

```
ggtaaagtcc aggacacagg actccagcct gctggccctg cctgtggggc cagcctgcgc      120
atctggtggc tcccccagca cctggcttat gcccccctcag gtacctggaa gctgtgagga    180
ggctgaaggt ggagggccac cggttcccca gaaccatcca catgaccttt gtgcctggta     240
ggagtggctc agatacctt gggaaagggg agggtggggc gggcagcct cctcatctca       300 ygtccctgct gcttttacag atgaggaggt tgggggtcac caaggcatgg agctgttcgt     360
gcagcggcct gagttccacg ccctgagggc aggctttgcc ctggatgagg gtgagcaggt     420
tggcaagcca atgagcagcc aggcaggag taggaggctg ctagtgggga ctgagctgct      480
ccaccctctg aaccccctt ccctcctcag gcatagccaa tcccactgat gccttcactg      540
tcttttatag tgagcggagt ccctggtgta agtatgagct tggagggagg gctcactcta     600
c                                                                    601

<210> SEQ ID NO 10
<211> LENGTH: 601
<212> TYPE: DNA
<213> ORGANISM: Homo sapiens

<400> SEQUENCE: 10
ccctgagggc aggctttgcc ctggatgagg gtgagcaggt tggcaagcca atgagcagcc      60 aggcaggag taggaggctg ctagtgggga ctgagctgct ccaccctctg aaccccctt      120 ccctcctcag gcatagccaa tcccactgat gccttcactg tcttttatag tgagcggagt    180
ccctggtgta agtatgagct tggagggagg gctcactcta caggcgggag gctaggccag    240
aaagggcacg gtcctatgca gggttgcaca gcaaagttga ggcctgagaa ggccttgaac    300
ycagggcctc tacctcccag ctctttccta tctgagcttc tctgagggca gccctgaat     360 gggcagaaac cagctgtatg ctacgggccc tgagtgggga caggaccctg ccagaggagc    420
ctggaatgag ggggagacct ggcccacccc aggctgattg tgtctccag ccctcaggc      480 tgaagacact gccttccccc tacacctccc cagggtgcg ggttaccagc actgggaggc    540
caggccatgc ctcacgcttc atggaggaca cagcagcaga gaagctggta cgtggcaccc    600
c                                                                    601

<210> SEQ ID NO 11
<211> LENGTH: 601
<212> TYPE: DNA
<213> ORGANISM: Homo sapiens

<400> SEQUENCE: 11
cagggcctct acctcccagc tctttcctat ctgagcttct ctgagggcaa gccctgaatg      60
ggcagaaacc agctgtatgc tacgggccct gagtggggac aggaccctgc cagaggagcc    120
tggaatgagg gggagacctg gcccacccca ggctgattg tgtctccagc ccctcaggct     180
gaagacactg ccttccccct acacctccc agggtgcgg gttaccagca ctgggaggcc     240
aggccatgcc tcacgcttca tggaggacac agcagcagag aagctggtac gtggcacccc    300
rggagggagt ctgggagttc aggaggctct atcctgaggc cactgtccca tttaacctca    360
tattctcata gcacaaggtt gtaaactcca tcctggcatt ccgggagaag gaatggcaga    420
ggtgaggcag cctgggaggc agtggggtgg ctctgggagg cggtaccaca gaggatagag    480
tctgagccac ctcttttatc tgttgctgcc gctaccctgc ccccacacca caggctgcag    540
tcaaaccccc acctgaaaga ggggtccgtg acctccgtga acctgactaa gctagagggt    600
g                                                                    601
```

<210> SEQ ID NO 12
<211> LENGTH: 601
<212> TYPE: DNA
<213> ORGANISM: Homo sapiens

<400> SEQUENCE: 12

```
ccagcactgg gaggccaggc catgcctcac gcttcatgga ggacacagca gcagagaagc      60
tggtacgtgg caccccagga gggagtctgg gagttcagga ggctctatcc tgaggccact     120
gtcccattta acctcatatt ctcatagcac aaggttgtaa actccatcct ggcattccgg     180
gagaaggaat ggcagaggtg aggcagcctg ggaggcagtg gggtggctct gggaggcggt     240
accacagagg atagagtctg agccacctct tttatctgtt gctgccgcta ccctgccccc     300
rcaccacagg ctgcagtcaa accccacct gaaagagggg tccgtgacct ccgtgaacct     360
gactaagcta gagggtggcg tggcctataa cgtgatacct gccaccatga cgccagctt     420
tgacttccgt gtggcaccgg atgtggactt caaggtgcca cctccacctg gtttggagg     480
agggatcctg gtcctcagt cttgtcctag aggcctctgg aaagcctgaa ggatcagctc     540
gtctcccttc tcttaggctt ttgaggagca gctgcagagc tggtgccagg cagctggcga     600
g                                                                    601
```

<210> SEQ ID NO 13
<211> LENGTH: 601
<212> TYPE: DNA
<213> ORGANISM: Homo sapiens

<400> SEQUENCE: 13

```
ctggagcctg agatcatgcc tgctgccact gacaaccgct atatccgcgc ggtgagccac      60
ttgcatatag tgcctgggca gtggactggg cctgagtgct ggcttttccc taacggctct     120
tcctcacccc tgcaggtggg ggtcccagct ctaggcttct cacccatgaa ccgcacacct     180
gtgctgctgc acgaccacga tgaacggctg catgaggctg tgttcctccg tggggtggac     240
atatatacac gcctgctgcc tgcccttgcc agtgtgcctg ccctgcccag tgacagctga     300
sccctggaac tcctaaacct ttgcccctgg gcttccatc ccaaccagtg ccaaggacct     360
cctcttcccc cttccaaata ataaagtcta tggacagggc tgtctctgaa gtactaacac     420
aaggacactc gtggagcaag aattttcctt ttcctgggga catgttacca tctccatttc     480
acagatgagg aaactgagcc tggctgttag cacttcccca ctaccccaca ctgctctgtg     540
cccccttgaca cagcacaccc attcagtacc atccagccat gtctgtgcct agcaagaaag     600
g                                                                    601
```

<210> SEQ ID NO 14
<211> LENGTH: 601
<212> TYPE: DNA
<213> ORGANISM: Homo sapiens

<400> SEQUENCE: 14

```
agagggccaa cggtgactgc tggctcctgt caaaacctgt acacccttgt gttggcagca      60
ggggccacag aggggcaggg tccctggtag actaggtcag ttcatcttag aggcctcagc     120
accctggatc tgtgtgtgca gaggcccagg aactgggctt tcatctcagc cttgctagga     180
ccccaggta gtaccaagag taaactatgg ccccagtagc agagcctgat ctagccagat     240
ctgctctatc ctgttctgac ttccctgagc atggggcagg agagacaggg ctgggtgggg     300
```

-continued

```
rtagttggat tttttaagtt tctagttgta gccagaagtc cagagcctgg ctctgggctg    360
caggcttagt actaatagaa ataacaatca ctcctgctca cagttgacaa ggagccagga    420
cttgactggc tttttttttt tttttttttt tttgagatgg agtctttctc tgtcgcccag    480
gctggcgtgc agtggcgcga tctcggctca ctgcaaactc cgcttcctgg gttcacgcca    540
ttctcctgcc tcagtttcct gagtagttgg gactacaggc cccgccacc acgcccagct     600 t                                                                    601
```

<210> SEQ ID NO 15
<211> LENGTH: 4
<212> TYPE: PRT
<213> ORGANISM: Homo sapiens

<400> SEQUENCE: 15

Asn Leu Thr Lys
 1

<210> SEQ ID NO 16
<211> LENGTH: 4
<212> TYPE: PRT
<213> ORGANISM: Homo sapiens

<400> SEQUENCE: 16

Asn Leu Thr Leu
 1

<210> SEQ ID NO 17
<211> LENGTH: 4
<212> TYPE: PRT
<213> ORGANISM: Homo sapiens

<400> SEQUENCE: 17

Ser His Thr Asp
 1

<210> SEQ ID NO 18
<211> LENGTH: 4
<212> TYPE: PRT
<213> ORGANISM: Homo sapiens

<400> SEQUENCE: 18

Thr Ala Ala Glu
 1

<210> SEQ ID NO 19
<211> LENGTH: 4
<212> TYPE: PRT
<213> ORGANISM: Homo sapiens

<400> SEQUENCE: 19

Thr Lys Leu Glu
 1

<210> SEQ ID NO 20
<211> LENGTH: 4
<212> TYPE: PRT
<213> ORGANISM: Homo sapiens

<400> SEQUENCE: 20

Thr Pro Thr Asp
 1

```
<210> SEQ ID NO 21
<211> LENGTH: 6
<212> TYPE: PRT
<213> ORGANISM: Homo sapiens

<400> SEQUENCE: 21

Gly Thr Asn Pro Thr Leu
1               5

<210> SEQ ID NO 22
<211> LENGTH: 6
<212> TYPE: PRT
<213> ORGANISM: Homo sapiens

<400> SEQUENCE: 22

Gly Gly His Gln Gly Met
1               5

<210> SEQ ID NO 23
<211> LENGTH: 10
<212> TYPE: PRT
<213> ORGANISM: Homo sapiens

<400> SEQUENCE: 23

Ile Leu Leu Asn Ser His Thr Asp Val Val
1               5                   10

<210> SEQ ID NO 24
<211> LENGTH: 40
<212> TYPE: PRT
<213> ORGANISM: Homo sapiens

<400> SEQUENCE: 24

Ala Gln Asp Met Lys Cys Val Ser Ile Gln Tyr Leu Glu Ala Val Arg
1               5                   10                  15

Arg Leu Lys Val Glu Gly His Arg Phe Pro Arg Thr Ile His Met Thr
            20                  25                  30

Phe Val Pro Asp Glu Glu Val Gly
        35                  40

<210> SEQ ID NO 25
<211> LENGTH: 6
<212> TYPE: PRT
<213> ORGANISM: Homo sapiens

<400> SEQUENCE: 25

Gly Val Ala Tyr Asn Val
1               5

<210> SEQ ID NO 26
<211> LENGTH: 10
<212> TYPE: PRT
<213> ORGANISM: Homo sapiens

<400> SEQUENCE: 26

Ile Leu Leu Asn Ser His Thr Asp Val Val
1               5                   10

<210> SEQ ID NO 27
<211> LENGTH: 40
<212> TYPE: PRT
<213> ORGANISM: Homo sapiens

<400> SEQUENCE: 27
```

-continued

```
Ala Gln Asp Met Lys Cys Val Ser Ile Gln Tyr Leu Glu Ala Val Arg
1               5                   10                  15

Arg Leu Lys Val Glu Gly His Arg Phe Pro Arg Thr Ile His Met Thr
            20              25                  30

Phe Val Pro Asp Glu Val Gly
            35          40
```

ISOLATED HUMAN AMINOACYLASE, NUCLEIC ACID MOLECULES ENCODING HUMAN AMINOACYLASE, AND USES THEREOF

RELATED APPLICATIONS

The present application is a divisional of U.S. application Ser. No. 09/814,951, filed on Mar. 23, 2001 and issued on May 14, 2002 as U.S. Pat. No. 6,387,661.

FIELD OF THE INVENTION

The present invention is in the field of enzyme proteins that are related to the aminoacylase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the aminoacylase subfamily.

The present invention has a substantial similarity to aminoacylase-1. Aminoacylase-1 (ACY1, EC 3.5.1.14), a new type of metalloprotein, is a cytosolic enzyme with a wide range of tissue expression and has been postulated to function in the catabolism and salvage of acylated amino acids. ACY-1 is more highly expressed in kidney than in liver. ACY1 has been assigned to chromosome 3p21, a region reduced to homozygosity in small-cell lung cancer and renal cell carcinoma, and shows a reduced or absent expression in small-cell lung cancer cell lines and tumors. For a review related to aminoacylase-1, see Miller et al., Genomics 1990 Sep.; 8(1):149–54, Mitta et al., J Biochem (Tokyo) 1992 Dec.; 112(6):737–42.

Enzyme proteins, particularly members of the aminoacylase subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the aminoacylase subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the aminoacylase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in the placenta, T cells from T cell leukemia, ovary, brain, lung and leukocyte.

DESCRIPTION OF THE FIGURE SHEETS

FIG. 1 provides the nucleotide sequence of a cDNA molecule sequence that encodes the enzyme protein of the present invention. (SEQ ID NO: 1) In addition, structure and functional information is provided, such as ATG start, stop and tissue distribution, where available, that allows one to readily determine specific uses of inventions based on this molecular sequence. Experimental data as provided in FIG. 1 indicates expression in humans in the placenta, T cells from T cell leukemia, ovary, brain, lung and leukocyte.

FIG. 2 provides the predicted amino acid sequence of the enzyme of the present invention. (SEQ ID NO: 2) In addition structure and functional information such as protein family, function, and modification sites is provided where available, allowing one to readily determine specific uses of inventions based on this molecular sequence.

FIG. 3 provides genomic sequences that span the gene encoding the enzyme protein of the present invention. (SEQ ID NO: 3) In addition structure and functional information, such as intron/exon structure, promoter location, etc., is provided where available, allowing one to readily determine specific uses of inventions based on this molecular sequence. As illustrated in FIG. 3, SNPs were identified at 10 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the aminoacylase subfamily. Utilizing these sequences, additional genomic sequences were assembled and transcript and/or cDNA sequences were isolated and characterized. Based on this analysis, the present invention provides amino acid sequences of human enzyme peptides and proteins that are related to the aminoacylase subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the aminoacylase subfamily and the expression pattern observed. Experimental data as provided in FIG. 1 indicates expression in humans in the placenta, T cells from T cell leukemia, ovary, brain, lung and leukocyte. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known aminoacylase family or subfamily of enzyme proteins.

Specific Embodiments

Peptide Molecules

The present invention provides nucleic acid sequences that encode protein molecules that have been identified as being members of the enzyme family of proteins and are related to the aminoacylase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in the placenta, T cells from T cell leukemia, ovary, brain, lung and leukocyte. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO: 2), for example, proteins encoded by the transcript/cDNA nucleic acid sequences shown in FIG. 1 (SEQ ID NO: 1) and the genomic sequences provided in FIG. 3 (SEQ ID NO: 3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO: 2), for example, proteins encoded by the transcript/cDNA nucleic acid sequences shown in FIG. 1 (SEQ ID NO: 1) and the genomic sequences provided in FIG. 3 (SEQ ID NO: 3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO: 2), for example, proteins encoded by the transcript/cDNA nucleic acid sequences shown in FIG. 1 (SEQ ID NO: 1) and the genomic sequences provided in FIG. 3 (SEQ ID NO: 3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. As indicated by the data presented in FIG. 3, the map position was determined to be on chromosome 3 by ePCR.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. As indicated by the data presented in FIG. 3, the map position was determined to be on chromosome 3 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

FIG. 3 provides information on SNPs that have been found in the gene encoding the enzyme protein of the present invention. SNPs were identified at 10 different nucleotide positions in introns and regions 5' and 3' of the ORF. Such SNPs in introns and outside the ORF may affect control/regulatory elements.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W.H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in the in the placenta, T cells from T cell leukemia, ovary, brain, lung detected by a virtual northern blot. In addition, PCR-based tissue screening panels indicate expression in leukocyte. A large percentage of pharmaceutical agents are being developed that modulate the activity of enzyme proteins, particularly members of the aminoacylase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the placenta, T cells from T cell leukemia, ovary, brain, lung and leukocyte. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the aminoacylase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in the in the placenta, T cells from T cell leukemia, ovary, brain, lung detected by a virtual northern blot. In addition, PCR-based tissue screening panels indicate expression in leukocyte.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in the placenta, T cells from T cell leukemia, ovary, brain, lung and leukocyte. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in the in the placenta, T cells from T cell leukemia, ovary, brain, lung detected by a virtual northern blot. In addition, PCR-based tissue screening panels indicate expression in leukocyte.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtiter plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in the placenta, T cells from T cell leukemia, ovary, brain, lung and leukocyte. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the placenta, T cells from T cell leukemia, ovary, brain, lung and leukocyte. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the placenta, T cells from T cell leukemia, ovary, brain, lung and leukocyte. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in the in the placenta, T cells from T cell leukemia, ovary, brain, lung detected by a virtual northern blot. In addition, PCR-based tissue screening panels indicate expression in leukocyte. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the placenta, T cells from T cell leukemia, ovary, brain, lung and leukocyte. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the placenta, T cells from T cell leukemia, ovary, brain, lung and leukocyte. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the placenta, T cells from T cell leukemia, ovary, brain, lung and leukocyte. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIGS. 1 or 3 (SEQ ID NO: 1, transcript sequence and SEQ ID NO: 3, genomic sequence), or any nucleic acid molecule that encodes the protein provided in FIG. 2, SEQ ID NO: 2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIGS. 1 or 3 (SEQ ID NO: 1, transcript sequence and SEQ ID NO: 3, genomic sequence), or any nucleic acid molecule that encodes the protein provided in FIG. 2, SEQ ID NO: 2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIGS. 1 or 3 (SEQ ID NO: 1, transcript sequence and SEQ ID NO: 3, genomic sequence), or any nucleic acid molecule that encodes the protein provided in FIG. 2, SEQ ID NO: 2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95 % or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 3 by ePCR.

FIG. 3 provides information on SNPs that have been found in the gene encoding the enzyme protein of the present invention. SNPs were identified at 10 different nucleotide positions in introns and regions 5' and 3' of the ORF. Such SNPs in introns and outside the ORF may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 10 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 3 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in the in the placenta, T cells from T cell leukemia, ovary, brain, lung detected by a virtual northern blot. In addition, PCR-based tissue screening panels indicate expression in leukocyte. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in the in the placenta, T cells from T cell leukemia, ovary, brain, lung detected by a virtual northern blot. In addition, PCR-based tissue screening panels indicate expression in leukocyte.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in the placenta, T cells from T cell leukemia, ovary, brain, lung and leukocyte. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in the in the placenta, T cells from T cell leukemia, ovary, brain, lung detected by a virtual northern blot. In addition, PCR-based tissue screening panels indicate expression in leukocyte. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in the placenta, T cells from T cell leukemia, ovary, brain, lung and leukocyte.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. FIG. 3 provides information on SNPs that have been found in the gene encoding the enzyme protein of the present invention. SNPs were identified at 10 different nucleotide positions in introns and regions 5' and 3' of the ORF. Such SNPs in introns and outside the ORF may affect control/regulatory elements. As indicated by the data presented in FIG. 3, the map position was determined to be on chromosome 3 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment. FIG. 3 provides information on SNPs that have been found in the gene encoding the enzyme protein of the present invention. SNPs were identified at 10 different nucleotide positions in introns and regions 5' and 3' of the ORF. Such SNPs in introns and outside the ORF may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in the in the placenta, T cells from T cell leukemia, ovary, brain, lung detected by a virtual northern blot. In addition, PCR-based tissue screening panels indicate expression in leukocyte. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS: 1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al, PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention. FIG. 3 provides information on SNPs that have been found in the gene encoding the enzyme protein of the present invention. SNPs were identified at 10 different nucleotide positions in introns and regions 5' and 3' of the ORF. Such SNPs in introns and outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al, *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, *Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufmnan et al., *EMBO J* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an nucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated polypeptide having an amino acid sequence comprising SEQ ID NO:2.

3. A composition comprising the polypeptide of claim 1 and a carrier.

4. A composition comprising the polypeptide of claim 2 and a carrier.

* * * * *